United States Patent
Millet

(10) Patent No.: US 11,806,324 B2
(45) Date of Patent: Nov. 7, 2023

(54) BETA-HYDROXYBUTYRIC ACID COMPOSITIONS AND METHODS FOR ORAL DELIVERY OF KETONE BODIES

(71) Applicant: AXCESS GLOBAL SCIENCES, LLC, Salt Lake City, UT (US)

(72) Inventor: Gary Millet, Salt Lake City, UT (US)

(73) Assignee: AXCESS GLOBAL SCIENCES, LLC, Salt Lake City, UT (US)

( * ) Notice: Subject to any disclaimer, the term of this patent is extended or adjusted under 35 U.S.C. 154(b) by 0 days.

(21) Appl. No.: 17/210,646

(22) Filed: Mar. 24, 2021

(65) Prior Publication Data

US 2021/0205241 A1 Jul. 8, 2021

Related U.S. Application Data

(63) Continuation-in-part of application No. 17/190,062, filed on Mar. 2, 2021, and a continuation-in-part of application No. 17/157,000, filed on Jan. 25, 2021, and a continuation-in-part of application No. 17/130,498, filed on Dec. 22, 2020, and a continuation-in-part of application No. 16/996,509, filed on Aug. 18, 2020, now Pat. No. 10,973,786, and a continuation-in-part of application No. 16/783,886, filed on Feb. 6, 2020, said application No. 17/190,062 is a continuation-in-part of application No. 16/783,956, filed on Feb. 6, 2020, and a continuation-in-part of application No. 16/783,997, filed on Feb. 6, 2020, and a continuation-in-part of application No. 16/783,844, filed on Feb. 6, 2020, now Pat. No. 11,103,470, said application No. 16/996,509 is a continuation-in-part of application No. 16/720,211, filed on Dec. 19, 2019, now Pat. No. 11,020,362, and a continuation-in-part of application No. 16/551,570, filed on Aug. 26, 2019, and a continuation-in-part of application No. 16/551,594, filed on Aug. 26, 2019, said application No. 17/157,000 is a continuation of application No. 16/381,202, filed on Apr. 11, 2019, now Pat. No. 10,925,843, said application No. 16/551,570 is a continuation-in-part of application No. 16/272,359, filed on Feb. 11, 2019, now Pat. No. 10,512,615, said application No. 16/551,594 is a continuation-in-part of application No. 16/272,328, filed on Feb. 11, 2019, now Pat. No. 10,980,772.

(60) Provisional application No. 63/070,532, filed on Aug. 26, 2020, provisional application No. 62/805,054, filed on Feb. 13, 2019, provisional application No. 62/769,432, filed on Nov. 19, 2018, provisional application No. 62/769,412, filed on Nov. 19, 2018, provisional application No. 62/760,462, filed on Nov. 13, 2018, provisional application No. 62/760,430, filed on Nov. 13, 2018, provisional application No. 62/723,274, filed on Aug. 27, 2018, provisional application No. 62/723,283, filed on Aug. 27, 2018, (Continued)

(51) Int. Cl.
*A61K 31/19* (2006.01)
*A61K 31/121* (2006.01)

(52) U.S. Cl.
CPC ............ *A61K 31/19* (2013.01); *A61K 31/121* (2013.01); *A23V 2200/3322* (2013.01)

(58) Field of Classification Search
CPC .......... A23V 2200/3322; A61K 31/121; A61K 31/19
See application file for complete search history.

(56) References Cited

U.S. PATENT DOCUMENTS

| | | |
|---|---|---|
| 2,238,149 A | 4/1941 | Aeckerle |
| 2,976,073 A | 3/1961 | Russell et al. |
| 4,627,808 A | 12/1986 | Hughes |

(Continued)

FOREIGN PATENT DOCUMENTS

| | | |
|---|---|---|
| CN | 86108978 A | 11/1987 |
| CN | 1256629 A | 6/2000 |

(Continued)

OTHER PUBLICATIONS

Blazquez et al. Journal of Neurochemistry, 1999, vol. 72 No. 4, pp. 1759-1768. (Year: 1999).*

(Continued)

*Primary Examiner* — Kara R McMillian
(74) *Attorney, Agent, or Firm* — Workman Nydegger

(57) ABSTRACT

Beta-hydroxybutyric acid compositions for oral delivery are substantially free of beta-hydroxybutyrate salts and are effective in rapidly raising blood ketone levels without causing acute acidosis or gastrointestinal (GI) distress when consumed in sufficiently dilute form and/or as a gel or suspension. By excluding beta-hydroxybutyrate salts (e.g., less than 1% by weight) containing alkali or alkaline earth metal ions, beta-hydroxybutyric acid solutions, gels, or suspensions can deliver exogenous ketone bodies without significantly altering electrolyte balance. Although aqueous beta-hydroxybutyric acid solutions are moderately acidic with a pH of about 3.5 to 4, when diluted with sufficient water, the water acts as a pseudo buffering agent that offsets otherwise harsh acidic effects when consumed orally. Gels and suspensions can also ameliorate acidic effects by partially encapsulating the beta-hydroxybutyric acid. Beta-hydroxybutyric acid can be enriched with the R- or the S-enantiomer, a racemic mixture, pure R-beta-hydroxybutyric acid, or pure S-beta-hydroxybutyric acid.

27 Claims, No Drawings

Related U.S. Application Data provisional application No. 62/659,564, filed on Apr. 18, 2018.

(56) References Cited

U.S. PATENT DOCUMENTS

| | | | |
|---|---|---|---|
| 4,771,074 A | 9/1988 | Lammerant et al. | |
| 4,997,976 A | 3/1991 | Brunengraber et al. | |
| 5,093,044 A | 3/1992 | Wretlind et al. | |
| 5,100,677 A | 3/1992 | Veech | |
| 5,116,868 A | 5/1992 | Chen et al. | |
| 5,288,512 A | 2/1994 | Seiden | |
| 5,292,774 A | 3/1994 | Hiraide et al. | |
| 5,654,266 A | 8/1997 | Chen et al. | |
| 5,700,670 A | 12/1997 | Yamagishi et al. | |
| 6,207,856 B1 | 3/2001 | Veech | |
| 6,217,915 B1 | 4/2001 | Luchansky et al. | |
| 6,232,345 B1 | 5/2001 | Hiraide et al. | |
| 6,316,038 B1 | 11/2001 | Veech | |
| 6,323,237 B1 | 11/2001 | Veech | |
| 6,380,244 B2 | 4/2002 | Martin et al. | |
| 6,613,356 B1 | 9/2003 | Vlahakos | |
| 6,706,756 B1 | 3/2004 | Fitzpatrick et al. | |
| 6,835,750 B1 | 12/2004 | Henderson | |
| 7,351,736 B2 | 4/2008 | Veech | |
| 7,807,718 B2 | 10/2010 | Hashim et al. | |
| 8,101,653 B2 | 1/2012 | Veech | |
| 8,124,589 B2 | 2/2012 | Henderson | |
| 8,426,468 B2 | 4/2013 | Henderson | |
| 8,642,654 B2 | 2/2014 | Clarke et al. | |
| 8,748,400 B2 | 6/2014 | Henderson | |
| 9,138,420 B2 | 9/2015 | D'Agostino et al. | |
| 9,211,275 B2 | 12/2015 | Clarke et al. | |
| 9,675,577 B2 | 6/2017 | D'Agostino et al. | |
| 9,717,767 B2 | 8/2017 | Carpenter et al. | |
| 9,795,580 B2 | 10/2017 | Weeber et al. | |
| 9,808,481 B2 | 11/2017 | Ritter et al. | |
| 9,925,164 B1 | 3/2018 | Hashim | |
| 9,957,246 B2 | 5/2018 | Stinchcomb et al. | |
| 10,022,409 B2 | 7/2018 | Carpenter et al. | |
| 10,051,880 B2 | 8/2018 | Clarke et al. | |
| 10,245,242 B1 | 4/2019 | Millet | |
| 10,245,243 B1 | 4/2019 | Millet | |
| 10,292,592 B2 | 5/2019 | Marshall et al. | |
| 10,292,952 B2 | 5/2019 | Millet | |
| 10,512,615 B1* | 12/2019 | Millet | A61K 47/10 |
| 10,588,876 B2 | 3/2020 | Millet | |
| 10,588,877 B2 | 3/2020 | Arnold | |
| 10,596,128 B2 | 3/2020 | Millet | |
| 10,596,129 B2 | 3/2020 | Millet | |
| 10,596,130 B2 | 3/2020 | Millet | |
| 10,596,131 B2 | 3/2020 | Millet | |
| 10,660,958 B2 | 5/2020 | Clarke | |
| 10,736,861 B2 | 8/2020 | Millet | |
| 10,792,269 B2 | 10/2020 | Hashim | |
| 10,925,843 B2 | 2/2021 | Millet | |
| 10,973,786 B2 | 4/2021 | Millet | |
| 10,980,764 B1 | 4/2021 | D'Agostino et al. | |
| 10,980,772 B2 | 4/2021 | Millet | |
| 11,020,362 B2 | 6/2021 | Millet | |
| 11,033,553 B2 | 6/2021 | Millet | |
| 11,103,470 B2 | 8/2021 | Millet | |
| 11,185,518 B2 | 11/2021 | Millet | |
| 11,202,769 B2 | 12/2021 | Millet | |
| 11,241,403 B2 | 2/2022 | Millet | |
| 2001/0014696 A1 | 8/2001 | Veech | |
| 2001/0041736 A1 | 11/2001 | Veech | |
| 2002/0013339 A1 | 1/2002 | Martin et al. | |
| 2003/0022937 A1 | 1/2003 | Veech | |
| 2004/0138293 A1 | 7/2004 | Werner et al. | |
| 2004/0266821 A1 | 12/2004 | Veech | |
| 2005/0129783 A1 | 6/2005 | McCleary et al. | |
| 2005/0169968 A1 | 8/2005 | Elmaleh et al. | |
| 2006/0275253 A1 | 12/2006 | Ushida et al. | |
| 2007/0029913 A1 | 2/2007 | Chen | |
| 2007/0135376 A1 | 6/2007 | Henderson | |
| 2007/0179197 A1 | 8/2007 | Henderson | |
| 2008/0058416 A1 | 3/2008 | Greenwood et al. | |
| 2008/0287372 A1 | 11/2008 | Henderson | |
| 2009/0253781 A1 | 10/2009 | Veech | |
| 2010/0041751 A1 | 2/2010 | Henderson | |
| 2010/0056631 A1* | 3/2010 | Hisamura | A61K 31/191 514/557 |
| 2010/0197758 A1 | 8/2010 | Andrews et al. | |
| 2010/0210726 A1 | 8/2010 | Kuriyama | |
| 2010/0298294 A1 | 11/2010 | Clarke et al. | |
| 2011/0237666 A1 | 9/2011 | Clarke et al. | |
| 2011/0287114 A1 | 11/2011 | Johnson | |
| 2012/0053240 A1 | 3/2012 | Rathmacher et al. | |
| 2012/0071548 A1 | 3/2012 | Veech | |
| 2012/0171165 A1 | 7/2012 | Buck et al. | |
| 2012/0202891 A1 | 8/2012 | Stinchcomb et al. | |
| 2013/0079406 A1 | 3/2013 | Veech | |
| 2013/0337116 A1 | 12/2013 | Petralia | |
| 2014/0256808 A1 | 9/2014 | Henderson | |
| 2014/0350105 A1 | 11/2014 | D'Agostino et al. | |
| 2015/0065571 A1* | 3/2015 | Clarke | A61K 31/22 514/546 |
| 2015/0132280 A1 | 5/2015 | Lopez et al. | |
| 2015/0320809 A1 | 11/2015 | Carpenter et al. | |
| 2016/0193173 A1 | 7/2016 | Clarke et al. | |
| 2016/0256411 A1 | 9/2016 | Aung-Din | |
| 2017/0020844 A1 | 1/2017 | Galinski | |
| 2017/0029650 A1 | 2/2017 | Veling et al. | |
| 2017/0172969 A1 | 6/2017 | D'Agostino et al. | |
| 2017/0258745 A1 | 9/2017 | Millet | |
| 2017/0266148 A1 | 9/2017 | D'Agostino et al. | |
| 2017/0290792 A1 | 10/2017 | Cavaleri | |
| 2017/0296501 A1 | 10/2017 | Lowery et al. | |
| 2017/0298339 A1 | 10/2017 | Hanson et al. | |
| 2017/0304564 A1 | 10/2017 | Dehaan et al. | |
| 2018/0021274 A1 | 1/2018 | Arnold | |
| 2018/0021281 A1 | 1/2018 | Berger | |
| 2018/0055797 A1 | 3/2018 | Llosa et al. | |
| 2018/0057846 A1 | 3/2018 | Llosa et al. | |
| 2018/0195096 A1 | 7/2018 | Veech et al. | |
| 2018/0214399 A1 | 8/2018 | Spector et al. | |
| 2019/0099394 A1 | 4/2019 | Ari et al. | |
| 2019/0151267 A1 | 5/2019 | Millet | |
| 2019/0167613 A1 | 6/2019 | Millet | |
| 2019/0167614 A1 | 6/2019 | Millet | |
| 2019/0177673 A1 | 6/2019 | Llosa et al. | |
| 2019/0183220 A1 | 6/2019 | Takada | |
| 2019/0183820 A1 | 6/2019 | Millet | |
| 2019/0183821 A1 | 6/2019 | Millet | |
| 2019/0191755 A1 | 6/2019 | Garvey et al. | |
| 2019/0209501 A1 | 7/2019 | Tinsley et al. | |
| 2019/0262293 A1 | 8/2019 | Millet | |
| 2019/0313682 A1 | 10/2019 | Nagel | |
| 2019/0321309 A1 | 10/2019 | Millet | |
| 2020/0078973 A1 | 3/2020 | Valeze et al. | |
| 2020/0140371 A1 | 5/2020 | Verdin et al. | |
| 2020/0268701 A1 | 8/2020 | D'Agostino et al. | |

FOREIGN PATENT DOCUMENTS

| | | |
|---|---|---|
| CN | 1347319 A | 5/2002 |
| CN | 1972698 A | 5/2007 |
| CN | 101969769 A | 2/2011 |
| CN | 102164884 A | 8/2011 |
| CN | 104224823 A | 12/2014 |
| CN | 105050594 A | 11/2015 |
| CN | 106038532 A | 10/2016 |
| CN | 106459646 A | 2/2017 |
| CN | 106858066 A | 6/2017 |
| EP | 1827412 A1 | 9/2007 |
| EP | 1915144 A2 | 4/2008 |
| EP | 2283834 A2 | 2/2011 |
| EP | 2976073 A1 | 1/2016 |
| EP | 3094321 A1 | 11/2016 |
| FR | 2997302 A1 | 5/2014 |
| JP | 11-060434 A | 3/1999 |
| JP | 2002-521330 A | 7/2002 |
| JP | 2004-035417 A | 2/2004 |
| JP | 2015-042644 A | 3/2015 |

(56) References Cited

FOREIGN PATENT DOCUMENTS

| | | |
|---|---|---|
| JP | 2015-514104 A | 5/2015 |
| JP | 2016-514725 A | 5/2016 |
| JP | 2016-121128 A | 7/2016 |
| JP | 2017-046688 A | 3/2017 |
| JP | 2020-502652 A | 1/2020 |
| JP | 2020-527583 A | 9/2020 |
| JP | 2021-504476 A | 2/2021 |
| JP | 2021-506294 A | 2/2021 |
| RU | 2345546 C2 | 2/2009 |
| WO | 87/03808 A1 | 7/1987 |
| WO | 98/41200 A1 | 9/1998 |
| WO | 03/70823 A2 | 8/2003 |
| WO | 2005/107724 A1 | 11/2005 |
| WO | 2006/061624 A1 | 6/2006 |
| WO | 2007/115282 A2 | 10/2007 |
| WO | 2008/005818 A1 | 1/2008 |
| WO | 2008/021394 A2 | 2/2008 |
| WO | 2008/024408 A2 | 2/2008 |
| WO | 2009/089144 A1 | 7/2009 |
| WO | 2010/021766 A1 | 2/2010 |
| WO | 2011/101171 A1 | 8/2011 |
| WO | 2013/150153 A1 | 10/2013 |
| WO | 2014/153416 A1 | 9/2014 |
| WO | 2015/071811 A1 | 5/2015 |
| WO | 2015/156865 A1 | 10/2015 |
| WO | 2016/123229 A1 | 8/2016 |
| WO | 2016/149687 A1 | 9/2016 |
| WO | 2017/156446 A1 | 9/2017 |
| WO | 2017/165443 A1 | 9/2017 |
| WO | 2017/165445 A1 | 9/2017 |
| WO | 2017/208217 A2 | 12/2017 |
| WO | 2018/055388 A1 | 3/2018 |
| WO | 2018/089863 A1 | 5/2018 |
| WO | 2018/114309 A1 | 6/2018 |
| WO | 2018/175879 A1 | 9/2018 |
| WO | 2018/187324 A1 | 10/2018 |
| WO | 2019/018683 A1 | 1/2019 |
| WO | 2019/204148 A1 | 10/2019 |
| WO | 2019/237152 A1 | 12/2019 |

OTHER PUBLICATIONS

National Center for Biotechnology Information. PubChem Compound Summary for CID 441, 3-Hydroxybutyric acid. https://pubchem.ncbi.nlm.nih.gov/compound/3-Hydroxybutyric-acid. (Year: 2005).*
A New Toy Measuring Blood Ketones. Diet Doctor, Aug. 21, 2012. Downloaded Apr. 1, 2015. http://www.dietdoctor.com/a-new-toy-measuring-blood-ketoones.
Arendash et al. "Caffeine and Coffee as Therapeutics Against Alzheimer's Disease", Journal of Alzheimer's Disease 20, 2010, S117-S126.
Arnold, Instant Ketosis?, (2013), Aug. 4, 2013 (retrieved on Apr. 21, 2017), p. 1-3. Retrieved from the internet; URL: < http://patrickarnoldblog.com/instant-ketosis/. (Year: 2013).
Bastin et al., "Salt Slection and Optimisation Procedures for Pharmaceutical New Chemical Entities", American Chemical Society and The Royal Society of Chemistry, vol. 4, No. 5, 2000, pp. 427-435.
Clarke, et al., Kinetics, safety and tolerability of (R)-3-hydroxybutyl (R)-3-hydroxybutyrate in healthy adult subjects. Regul Toxicol Pharmacol. Aug. 2012;63(3):401-8.
Cresci, G. et al., Lactobacillus GG and Tributyrin Supplementation Reduce Antibiotic-Induced Intestinal Injury, 2013, Journal of Parenteral and Enteral Nutrition, 37(6), 1-20 (Year: 2013).
Dietary Guidelines Recommendations at https://health.gov/our-work/food-nutrition/2015-2020-dietary-guidelines/guidelines/ appendix-7/ (2010) (retrieved from the internet Oct. 20, 2020) (Year: 2010).
Dolson, Laura. How to Test Your Blood for Ketones. Downloaded Apr. 1, 2015. http://lowcarbdiets.about.com/od/KetogenicDiets/a/How-to-Test-Blood-For-Ketones.htm.

Extended European Search Report issued in PCT/US2017021886 dated Oct. 17, 2019.
First Examination Report for New Zealand Patent Application No. 711433 issued by the New Zealand Intellectual Property Office dated Mar. 10, 2016.
First Office Action issued by the Chinese State Intellectual Property Office dated Nov. 4, 2016 for corresponding Chinese Patent Application No. 201480016818.0.
Hashim, Sarni A., et al., "Ketone body therapy: from the ketogenic diet to the oral administration of ketone ester", Journal of Lipid Research, vol. 55, 2014.
Haywood A, Glass BD. Pharmaceutical excipients—where do we begin? Australian Prescriber. 2011; 34: 112-114.
Henderson, Samuel T. "Ketone Bodies as a Therapeutic for Alzheimer's Disease." Neurotherapeutics. Jul. 2008;5(3):470-80.
Holtzman et al., "Role of adenosine receptors in caffeine tolerance", J. Pharmacol. Exp. Ther., 1991 ;256(1 ):62-68.
Ichim, T. et al., Experimental support for the effects of a probiotic/digestive enzyme supplement on serum cholesterol concentrations and the intestinal microbiome, 2016, Journal of Translational Medicine, 14(184), 1-9 (Year: 2016).
International Preliminary Report on Patentability received for PCT Patent Application No. PCT/US2019/048364, dated Mar. 11, 2021, 7 pages.
International Search Report and Written Opinion issued in PCT/US19/48357 dated Nov. 18, 2019.
International Search Report and Written Opinion issued in PCT/US19/48364 dated Nov. 15, 2019.
International Search Report and Written Opinion issued in PCT/US20/16952 dated Apr. 22, 2020.
International Search Report and Written Opinion issued in PCT/US20/17552 dated May 4, 2020.
International Search Report and Written Opinion issued in PCT/US20/17555 dated May 4, 2020.
International Search Report and Written Opinion issued in PCT/US20/17556 dated May 4, 2020.
International Search Report and Written Opinion received for PCT Patent Application No. PCT/US20/37289, dated Sep. 30, 2020, 8 pages.
International Search Report and Written Opinion received for PCT Patent Application No. PCT/US2020/033159, dated Aug. 12, 2020, 9 pages.
International Search Report and Written Opinion received for PCT Patent Application No. PCT/US21/17078, dated Apr. 23, 2021, 9 pages.
International Search Report cited in PCT/US18/62093 dated Feb. 1, 2019.
International Search Report cited in PCT/US19/27214 dated Jun. 25, 2019.
It Really is in Your Blood: Glucose to Ketone Ratios. Greymadder, Sep. 15, 2014. Downloaded Apr. 1, 2015. http://greymadder.net/2014/09/15/it-really-is-in-your-blood-glucose-to-ketone-ratios/.
James, "Optical Purity and Enantiomeric Excess" at https://www.masterorganicchemistry.com/2017/02/24/optical-purity-and-enantiomeric-excess/. (Retrieved from the internet Nov. 6, 2018) (Year: 2018).
Karppanen et al, J. Human Hypertension (2005), vol. 19, pp. S10-S19. (Year: 2005).
Kesl, et al., "Effects of exogenous ketone supplementation on blood ketone, glucose, triglyceride, and lipoprotein levels in Spraque-Dawley rats", Nutrition & Metabolism (2016).
Kirsch, Jretal. "Butanediol Induced Ketosis Increases Tolerance to Hypoxia in the Mouse." Stroke. 1980, vol. 11, No. 3, pp. 506-513.
Kossoff, Eric H. et al. "Optimal Clinical Management of Children Receiving the Ketogenic Diet: Recommendations of the International Ketogenic Diet Study Group." Epilepsia, Feb. 2009;50(2):304-17. Epub Sep. 23, 2008.
Krotkiewski, "Value of VLCD Supplementation with Medium Chain Triglycerides", Int J Obes Relat Metab Disord, Sep. 2001, 25(9), pp. 1393-1400.
Malo, M. S. et al., Intestinal alkaline phosphatase preserves the normal homeostasis of gut microbiota, 2010, Gut, 59, 1476-1484 (Year: 2010).

(56) References Cited

OTHER PUBLICATIONS

Murray, Andrew J., et al. "Novel ketone diet enhances physical and cognitive performance", The FASEB Journal, Vo. Dec. 30, 2016.
Nova Max Plus Glucose and Ketone Testing with One Monitor. Downloaded Apr. 1, 2015. http://www.novacares.com/nova-max-plus/.
Parker, Steve, "Ketogenic Mediterranean Diet: Version 2.3," Nov. 23, 2010, pp. 1-3. (Year: 2010).
PCT International Search Report and Written Opinion issued by the International Searching Authority dated Jul. 15, 2014 or International Patent Application No. PCT/US2014/031237.
Precision Xtra vs. NovaMax Plus: Ketone Meter Evaluation. Jimmy Moore's Livin' La Vida Low Garb Blog. Downloaded Apr. 1, 2015. http://livinlavidalowcarb.com/blog/precision-xtra-vs-novamax-plus-ketone-meter-evaluation/15918.
Pubchem, "Acetoacetic acid" Electronic Resource: https://pubchem.ncbi.nim.nih.gov/compound/Acetoacetic-acid, Retrieved on Sep. 3, 2019.
Robson et al. Expert Opin. Drug Saf. (2011), vol. 10, pp. 675-685 (Year: 2011).
Roeder, Lois M., et al. The Effects of Ketone Bodies, Bicarbonate, and Calcium on Hepatic Mitochondrial Ketogenesis. Archives of Biochemistry and Biophysics, vol. 217, No. 2, Sep. pp. 460-467, 1982.
Sajewicz et al. in Journal of Liquid Chromatography & Related Technologies, 33:1047-1057 (2010) (Year: 2010).
Serum Ketones Test. MedlinePlus Medical Encyclopedia. Downloaded Apr. 1, 2015. http://www.nlm.nih.gov/medlineplus/ency/article/003498.htm.
Shigeno etal. in Biosci. Biotech. Biochem., 56(2), 320-323 (1992) (Year: 1992).
Tanaka, J., et al., "Significance of Blood Ketone Body Ration as an indicator of Hepatic Cellular Energy Status in Jaundiced Rabbits", Gastroenterology, 1979, vol. 76, No. 4, pp. 691-696.
Tisdale, "Reduction of weight loss and tumour size in a cachexia model by a high fat diet", British Journal of Cancer, Jul. 1987, vol. 56, p. 39-43.
Vandenberghe et al. in Can. J. Physiol. Pharmacol. 95: 455-458 (2017) (Published at www.nrcresearchpress.com/cjpp on Nov. 25, 2016). (Year: 2016).
Veech, et al., "Ketone Bodies Mimic the Life Span Extending Properties of Caloric Restriction", IUBMB Life Feb. 8, 2017.
Veech, Richard L. "The Therapeutic Implications of Ketone Bodies: The Effects of Ketone Bodies in Pathological Conditions: Ketosis, Ketogenic Diet, Redox States, Insulin Resistance, and Mitochondrial Metabolism." Prostaglandins Leukot Essent Fatty Acids. Mar. 2004;70(3):309-19.
Vorgerd, M. And J. Zange. Treatment of glycogenosys type V (McArdle disease) with creatine and ketogenic diet with clinical scores and with 31P-MRS on working leg muscle. Acta Myologica, 2007; XXVI; pp. 61-63.
Acetoacetate, Acetone, and Dibenzylamine (A Contaminant in L-(+)-Beta-Hydroxybutyrate) Exhibit Direct Anticonvulsant Actions in Vivo, Epilepsia, Raven Press Ltd, New York, US, vol. 43, No. 4, Apr. 1, 2002 (Apr. 1, 2002), pp. 358-361.
Haces M L et al: "Antioxidant capacity contributes to protection of ketone bodies against oxidative damage induced during hypoglycemic conditions", Experimental Neurology, Elsevier, Amsterdam, NL, vol. 211, No. 1, May 1, 2008 (May 1, 2008), pp. 85-96.
Stubbs et al., "On the Metabolism of Exogenous Ketones in Humans", frontiers in Physiology, vol. 8, 2017, 13 pages.
Tsai et al., "Stereoselective effects of 3-hydroxybutyrate on glucose utilization of rat cardiomyocytes" life Sciences 78(2006) pp. 1385-1391.
Craciun, S. et al. Microbial conversion of choline to trimethylamine requires a glycyl radical enzyme, 2012, PNAS, 109(52): 21307-21312 (Year: 2012).
International Preliminary Report on Patentability received for PCT Patent Application No. PCT/US2020/016952, dated Aug. 26, 2021, 7 pages.
International Preliminary Report on Patentability received for PCT Patent Application No. PCT/US2020/017552, dated Aug. 26, 2021, 7 pages.
International Preliminary Report on Patentability received for PCT Patent Application No. PCT/US2020/017555, dated Aug. 26, 2021, 7 pages.
International Preliminary Report on Patentability received for PCT Patent Application No. PCT/US2020/017556, dated Aug. 26, 2021, 7 pages.
International Search Report and Written Opinion received for PCT Patent Application No. PCT/US20/017555, dated May 4, 2020, 8 pages.
Amazon, "Perfect Keto Perform Pre Workout Powder—Burn Fat for Fuel Energy Supplement Drink Mix for Men and Women—Keto Friendly with Ketone Salts, BCAA, Nitric Oxide & MCT", Sep. 25, 2017 entire document especially p. 1 Retrieved from https://www.amazon.com/Perfect-Keto-Perform-PreworkoutSupplement/dp/B0751379Q9/ref=sr_1_9?dchild=1&keywords=ketone+pre+workout&qid=1597938465&sr=8-9.
Extended European Search Report received for EP Patent Application No. 19788264.0, dated Dec. 20, 2021, 11 pages.
International Preliminary Report on Patentability received for PCT Patent Application No. PCT/US20/37289, dated Dec. 30, 2021, 6 pages.
International Preliminary Report on Patentability received for PCT Patent Application No. PCT/US2020/033159, dated Nov. 25, 2021, 6 pages.
International Search Report and Written Opinion received for PCT Patent Application No. PCT/US21/045186, dated Nov. 22, 2021, 10 pages.
Kim Do Young et al., "Ketone bodies are protective against oxidative stress in neocortical neurons," Journal of Neurochemistry, vol. 101, Issue 5, Jun. 1, 2007, pp. 1316-1326.
Maalouf Met al., "Ketones inhibit mitochondrial production of reactive oxygen species production following glutamate excitotoxicity by increasing NADH oxidation," Neuroscience, New York, NY, US, vol. 145, Issue 1, Mar. 2, 2007, pp. 256-264.
Maalouf Met al., "The neuroprotective properties of calorie restriction, the ketogenic diet, and ketone bodies," Brain Research Reviews, Elsevier, NL, vol. 59, No. 2, Mar. 1, 2009, pp. 293-315.
Pete J Cox et al., "Acute nutritional ketosis: implications for exercise performance and metabolism," Extreme Physiology & Medicine, vol. 3, Issue 1, Dec. 1, 2014, pp. 1-9.
Grootaert, C. Comparison of prebiotic effects of arabinoxylan oligosaccharides and inulin in a simulator of the human intestinal microbial ecosystem, 2009, FEMS Microbiology Ecology, 69: 231-242 (Year: 2009).
Holscher, H. Dietary fiber and prebiotics and the gastrointestinal microbiota, 2017, Gut Microbes, 8(2): 172-184 (Year: 2017).
International Search Report and Written Opinion received for PCT Patent Application No. PCT/US2021/063559, dated Mar. 18, 2022, 9 pages.
Lile et al. Drug Alcohol Depend. 2012, 122 (1-2), 61-69.
Parker, Steve, "Ketogenic Mediterraanean Diet: Version 2.3," Nov. 23, 2010, pp. 1-3. (Year: 2010).
Sanchez, J. I. et al. Arabinoxylan oligosaccharides (AXOS) affect the protein/carbohydrate fermentation balance and microbial population dynamics of the Simulator of Human Intestinal Microbial Ecosystem, 2009, Microbial Biotechnology, 2(1): 101-113 (Year: 2009).
Walton, G. et al. A randomised, double-blind, placebo controlled cross over study to determine the gastrointestinal effects of consumption of arabinoxylan-oligosaccharides enriched bread in healthy volunteers, 2012, Nutrition Journal, 11(36): 1-11 (Year: 2012).
European Search Report received for EP Patent Application No. 20755289.4, dated Oct. 11, 2022, 7 pages.
European Search Report received for EP Patent Application No. 20755994.9, dated Sep. 21, 2022, 6 pages.
Extended European Search Report received for EP Patent Application No. 20755770.3, dated Sep. 1, 2022, 7 pages.
International Preliminary Report on Patentability received for PCT Patent Application No. PCT/US2021/017078, dated Aug. 18, 2022, 7 pages.

(56) References Cited

OTHER PUBLICATIONS

John C Newman et al: "beta-Hydroxybutyrate: A Signaling Metabolite", Annual Review of Nutrition, vol. 37, Aug. 21, 2017 (Aug. 21, 2017), pp. 51-76, XP055771586.
Slavin, J. Fiber and Prebiotics: Mechanisms and Health Benefits, 2013, Nutrients, 5: 1417-1425 (Year: 2013).
The Medical Republic, 2018, Sustained Release Sodium Butyrate Supplement Now Available to Support Management of GI Disorders, https://medicalrepublic.com.au/sustained-release-sodium-butyrate-supplement-now-available-support-management-gi-disorders/15791; newly cited (Year: 2018).
Zaleski, A. et al., Butyric acid in irritable bowel syndrome, 2013, Prz Gastroenterol, 8(6), 350-353 (Year: 2013).
European Search Report received for EP Patent Application No. 20805593.9, dated Dec. 16, 2022, 9 pages.
Maguire et al., "Gut dysbiosis, leaky gut, and intestinal epithelial proliferation in neurological disorders: towards the development of a new therapeutic using amino acids, prebiotics, probiotics, and postbiotics", Rev Neurosci . Jan. 28, 2019, vol. 30, No. 2, pp. 179-201.
Rich A.J., "Ketone Bodies as Substrates," Proceedings of the Nutrition Society (1990), vol. 49, 361-373.
Wu et al., "Medium-Chain Triglycerides in Infant Formulas and Their Relation to Plasma Ketone Body Concentrations," Pediatric Research, vol. 20, No. 4, (1986), pp. 338-341.
Yang Y. et al., Role of Adherent-Invasive *Escherichia coli* in Inflammatory Bowel Disease, Letters in Biotechnology , No. 06, Nov. 30, 2016.
Anonymous: "Blue Lemon Ice Advanced Formula", MINTEL, Database accession No. 4315637, 2016, pp. 3.
Anonymous: "Strawberry Pineapple Flavour Pre-Exertion Performance Optimizer", MINTEL, Database accession No. 5661617, 2018, pp. 4.
Bala et al. Drug Invention Today. Jun. 1, 2018;10(6), 929-931.
Budin. N. et al., "Efficient synthesis of the ketone body ester (R)-3-hydroxybutyryl-(R)-3-hydroxybutyrate and its (S, S) enantiomer," Bioorganic Chemistry, vol. 80, Oct. 2018, pp. 560-564.
Huang Dexiang et al., "Clinical Intravenous Nutrition", Shanghai Medical University Press Jan. 31, 1994, pp. 121-124.
International Preliminary Report on Patentability received for PCT Patent Application No. PCT/US2018/062093, dated Jun. 4, 2020, 6 pages.
International Preliminary Report on Patentability received for PCT Patent Application No. PCT/US2021/045186, dated Mar. 9, 2023, 7 pages.
International Preliminary Report on Patentability received for PCT Patent Application No. PCT/US2021/050302, dated Mar. 2, 2023, 8 pages.
International Preliminary Report on Patentability received for PCT Patent Application No. PCT/US2021/063559, dated Jul. 6, 2023, 6 pages.
Kaster M.P. et al, "Caffeine acts through neuronal adenosine A2A receptors to prevent mood and memory dysfunction triggered by chronic stress", Proceedings of the National Academy of Sciences, vol. 112, No. 25, Jun. 8, 2015, pp. 7833-7838.
Lonza, Duocap Capsules, Feb. 16, 2018, https ://web .archive.org/web/20180216001656/https://www.capsugel.com/consumer-health-nutrition-products/duocap-capsules (Year: 2018).
Luis Villasenor, "Supplements and Ketogenic Diets—Facts and Myths", Retrieved from https://www.ketogains.com/2015/09/supplements-and-ketogenic-diets-facts-and-myths/, Sep. 18, 2015, pp. 15.
Lytra. G. et al., "Distribution and Organoleptic Impact of Ethyl 3-Hydroxybutanoate Enantiomers in Wine," J. Agric. Food Chem, vol. 63, Issue 48, 2015, pp. 10484-10491.
Mangels D.R. et al, "Catechins as Potential Mediators of Cardiovascular Health", Translational Sciences, vol. 37, No. 5, May 1, 2017, pp. 757-763.
Sorensen et al. ("Simultaneous determination of B-hydroxybutyrate and B-hydroxy-B-methylbutyrate in human whole blood using hydrophilic interaction liquid chromatography electrospray tandem mass spectrometry", Clinical Biochemistry, 2013, vol. 46, pp. 1877-1883) (Year: 2013).
Sorensen et al. ("Simultaneous determination of β-hydroxybutyrate and β-hydroxy-β-methylbutyrate in human whole blood using hydrophilic interaction liquid chromatography electrospray tandem mass spectrometry", Clinical Biochemistry, 2013, vol. 46, pp. 1877-1883) (Year: 2013).
O'Meara, Cyndi, Changing Habits, Ketosis—Can we achieve it in a pill?, https://changinghabits. com.au/ketosis-can-we-achieve-it-in-a-pill/, 12 pages, (Jan. 13, 2017).
Sara, How do you know which product is right for you? How to choose exogenous ketones, https://ketosupplements.co.uk/how-to-choose-exogenous-ketones/, 10 pages, (Sep. 25, 2017).
Short, Jay, Effects of A Ketone/Caffeine Supplement On Cycling and Cognitive Performance, Master's thesis, Ohio State University, 61 pages, (Jan. 1, 2017).

* cited by examiner

BETA-HYDROXYBUTYRIC ACID COMPOSITIONS AND METHODS FOR ORAL DELIVERY OF KETONE BODIES

CROSS-REFERENCE TO RELATED APPLICATIONS

This application is a continuation-in-part of U.S. patent application Ser. No. 17/157,000, filed Jan. 25, 2021, which is a continuation of U.S. patent application Ser. No. 16/381,202, filed Apr. 11, 2019, now issued U.S. Pat. No. 10,925,843, which claims the benefit of U.S. Prov. App. No. 62/659,564, filed Apr. 18, 2018.

This application is also a continuation-in-part of U.S. patent application Ser. No. 17/130,498, filed Dec. 12, 2020, and is a continuation-in-part of U.S. patent application Ser. No. 16/996,509, filed Aug. 18, 2020, which is a continuation-in-part of U.S. patent application Ser. No. 16/720,211, filed Dec. 19, 2019, and is also a continuation-in-part of U.S. patent application Ser. No. 16/783,844, filed Feb. 6, 2020, and a continuation-in-part of U.S. patent application Ser. No. 16/783,886, filed Feb. 6, 2020, and a continuation-in-part of U.S. patent application Ser. No. 17/190,062, filed Mar. 2, 2021, which is a continuation-in-part of U.S. patent application Ser. No. 16/783,956, filed Feb. 6, 2020, which claims the benefit of U.S. Prov. App. No. 62/805,054, filed Feb. 13, 2019, and is also a continuation-in-part of U.S. patent application Ser. No. 16/783,997, filed Feb. 6, 2020, and a continuation-in-part of U.S. patent application Ser. No. 16/551,570, filed Aug. 26, 2019, which is a continuation-in-part of U.S. patent application Ser. No. 16/272,359, filed Feb. 11, 2019, now issued U.S. Pat. No. 10,512,615, which claims the benefit of U.S. Prov. App. No. 62/769,412, filed Nov. 19, 2018, U.S. Prov. App. No. 62/760,430, filed Nov. 13, 2018, and U.S. Prov. App. No. 62/723,274, filed Aug. 27, 2018, and is also a continuation-in-part of U.S. patent application Ser. No. 16/551,594, filed Aug. 26, 2019 which is a continuation-in-part of U.S. patent application Ser. No. 16/272,328, filed Feb. 11, 2019, which claims the benefit of U.S. Prov. App. No. 62/769,432, filed Nov. 19, 2018, U.S. Prov. App. No. 62/760,462, filed Nov. 13, 2018, and U.S. Prov. App. No. 62/723,283, filed Aug. 27, 2018.

This application also claims the benefit of U.S. Prov. App. No. 63/070,532, filed Aug. 26, 2020.

The foregoing patents and applications are incorporated by reference in their entirety.

BACKGROUND

1. Field of the Invention

The invention relates to aqueous drinks, liquid and powder drink additives, and liquid and powder food additives containing beta-hydroxybutyric acid and methods for delivering exogenous ketone bodies to a subject in need thereof.

2. Related Technology

In periods of fasting, extreme exercise, and/or low carbohydrate consumption, glucose and glycogen stores in the body are rapidly used and can become quickly depleted. As glucose stores are depleted, the body metabolically shifts to creation of ketone bodies for energy. Ketone bodies can be used by cells of the body as fuel to satisfy the body's energy needs. During prolonged fasting, for example, blood ketone levels can increase to 2-3 mmol/L or more. It is conventionally understood that when blood ketones rise above 0.5 mmol/L, the heart, brain, and peripheral tissues use ketone bodies (e.g., beta-hydroxybutyrate and acetoacetate) as the primary fuel source. This condition is referred to as "ketosis". Between 1.0 mmol/L and 3.0 mmol/L the condition is called "nutritional ketosis."

Upon transitioning into ketosis, i.e., during ketogenic metabolism in the liver, the body uses dietary and bodily fats as a primary energy source. Consequently, when in ketosis, one can induce loss of body fat by controlling dietary fat intake and maintaining low carbohydrate intake and blood level to sustain ketosis.

While in ketosis, the body is in ketogenesis and is essentially burning fat for its primary fuel. The body cleaves fats into fatty acids and glycerol and transforms fatty acids into acetyl CoA molecules, which are transformed through ketogenesis into the water-soluble ketone bodies beta-hydroxybutyrate ("β-hydroxybutyrate" or "beta-hydroxybutyrate"), acetoacetate, and acetone in the liver. Beta-hydroxybutyrate and acetoacetate are used by the body for energy, while acetone is removed as a by-product of ketogenesis.

The metabolism of ketone bodies is associated with several improvements to metabolic function, such as anti-convulsant effects, enhanced metabolism by the brain, neuroprotection, muscle sparing properties, improved cognitive and physical performance, and epigenetic effects (positive or beneficial gene expressions). Science-based improvements in efficiency of cellular metabolism, managed through ketone supplementation, can have beneficial impacts on physical, cognitive health, and psychological health, and a long-term impact on health with respect to the common avoidable diseases such as obesity, cardiovascular disease, neurodegenerative diseases, diabetes, and cancer.

Ketone bodies are most often administered as salts or esters. Ketone salts are generally safe but can introduce excessive quantities of electrolytes when consumed in excess. Ketone esters do not contribute electrolytes but must be hydrolyzed before they are usable as ketone bodies. Downsides of ketone esters is they can have unpleasant taste and introduce alcohol into the body when hydrolyzed.

Free acid forms of beta-hydroxybutyrate and acetoacetate are used less frequently. It has been reported that solutions of racemic beta-hydroxybutyric acid have been administered intravenously. Dilute solutions are required when ketone body acids are delivered intravenously to prevent negative effects of low pH and isotonic deficiency. For example, a 1 mmol/L beta-hydroxybutyric acid solution contains only 0.0104% w/v of ketone bodies. Such solutions are useless for oral delivery of ketone bodies because one would have to consume approximately 10 liters to obtain 1 gram of ketone bodies.

Some have proposed oral delivery of ketone bodies as partially buffered acid compositions. For example, US Pub. No. 2018/0057846 (Llosa et al.) discloses solutions containing partially buffered enantiomerically pure or enriched D-beta-hydroxybutyrate compositions with up to at most 99% free acid and at least 1% ketone salt. Llosa et al. further teach that "[t]he use of pure, free acid form of β-HB at the upper limit of therapeutic doses has been considered undesirable due to the possibility of acute acidosis or gastrointestinal (GI) distress" and "the O-hydroxy group is unstable in the presence of low pH" (paragraph [0035]). US Pub. No. US 2018/0021274 (Arnold et al.) discloses compositions containing beta-hydroxybutyric acid and beta-hydroxybutyrate salt in ratios of up to "~125 parts free acid per ~7 parts salt" (paragraph [0019]), which equates to a free acid concentration of up to about 94.7% by weight and a salt concentration of at least about 5.3% by weight.

SUMMARY

It has been unexpectedly found that aqueous beta-hydroxybutyric acid compositions for oral delivery that are free or substantially free of beta-hydroxybutyrate salts are effective in rapidly raising blood ketone levels without causing acute acidosis or gastrointestinal (GI) distress when consumed in sufficiently dilute form. In the absence of significant quantities of beta-hydroxybutyrate salts containing alkali or alkaline earth metal ions, aqueous beta-hydroxybutyric acid solutions can deliver exogenous ketone bodies without significantly altering electrolyte balance. By providing aqueous beta-hydroxybutyric acid at a concentration within specific ranges, it is possible to maintain beta-hydroxybutyric acid stability and prevent self-esterification and precipitation.

In some embodiments, aqueous beta-hydroxybutyric acid solutions can have a concentration that is sufficiently diluted such that volumes of about 4 oz. (about 120 ml) to about 16 oz. (about 475 ml) can deliver a quantity of ketone bodies in a range of about 0.5 gram to about 25 grams, without harming the stomach or causing significant acidosis. For example, dilute aqueous beta-hydroxybutyric acid solutions can have a concentration of beta-hydroxybutyric acid in a range of about 0.4% w/v to about 6% w/v. Although aqueous beta-hydroxybutyric acid solutions are moderately acidic, with a pH of about 3.5 to 4, when diluted with sufficient water, the water itself acts as a pseudo buffering agent that offsets the otherwise harsh effects of the acid when consumed orally.

In some embodiments, aqueous beta-hydroxybutyric acid solutions can be provided as a concentrate for later dilution by the user, such as with water, juice, drink, energy shot, or other aqueous composition to a concentration in a range of about 0.4% w/v to about 6% w/v. Concentrated solutions may comprise beta-hydroxybutyric acid in a range of about 6% w/v to about 60% w/v and then diluted by the user as desired, such as from about 2 to about 30 times, with water, juice, drink, or other aqueous composition, as desired. Preferably, the aqueous beta-hydroxybutyric acid solutions will not be so concentrated so as to self-polymerize and form significant amounts of precipitates, although it should be understood that such polymerized precipitates are harmless when consumed with sufficient water but lack the efficacy of the monomeric form of beta-hydroxybutyric acid.

In some embodiments, concentrated or dilute beta-hydroxybutyric acid solutions can be manufactured by combining a powder or other solid form of beta-hydroxybutyric acid with water, drink, beverage, sauce, gel, or other liquid or semi-liquid drink, energy product, or food product. When the beta-hydroxybutyric acid solution, drink, sauce, or gel is prepared by a user, the powder or other solid form of beta-hydroxybutyric acid can be flavored and may contain other additives, such as one or more of stabilizer, vitamin, mineral, stimulant, nootropic, vasodilator, cannabinoid, amino acid, and the like. The powder may be provided in individual pre-dosed packets, pouches, tablets, or capsules, or it may be provided in a kit with a measuring device configured to measure out a predetermined dose or fraction thereof. A plurality (e.g., 2 or 3) of dissolvable tablets representing a single dose can be packaged together in a packet, pouch, or other container. In some embodiments, a dissolvable tablet may be effervescent and fizz when added to water. In the case of an effervescent tablet, it may be desirable to include a quantity of an edible acid (e.g., citric or malic) together with a bicarbonate or carbonate salt to provide the desired effervescent action yet provide less than 1% of total beta-hydroxybutyrate salt(s) upon dissolution in water (i.e., if the edible acid has a lower pKa than beta-hydroxybutyric acid a salt of the edible acid will form preferentially over beta-hydroxybutyrate salt).

Beta-hydroxybutyric acid compositions are free or substantially free of beta-hydroxybutyrate salts so as to contain less than 1% of one or more beta-hydroxybutyrate salts by combined weight of beta-hydroxybutyric acid and beta-hydroxybutyrate salt(s). In currently preferred embodiments, beta-hydroxybutyric acid compositions are essentially or totally free of beta-hydroxybutyrate salts, i.e., contain 0% by weight of beta-hydroxybutyrate salts.

In some embodiments, the beta-hydroxybutyric acid compositions may contain one or more nutritionally or pharmaceutically acceptable carriers or additives in addition to water. For example, beta-hydroxybutyric acid compositions may optionally include at least one additive selected from acetoacetic acid, 1,3-butanediol, beta-hydroxybutyrate esters, vitamins, minerals, central nervous system stimulants, nootropics, edible acids, amino acids, muscle-promoting compounds (e.g., beta-hydroxy beta-methylbutyrate), one or more cannabinoids (e.g., tetrahydrocannabinol and/or cannabidiol), and the like.

In various embodiments, beta-hydroxybutyric acid compositions may include enantiomerically pure R-beta-hydroxybutyric acid, enantiomerically pure S-beta-hydroxybutyric acid, a racemic mixture of R- and S-beta-hydroxybutyric acid (i.e., a mixture having a 1:1 enantiomeric ratio of R-beta-hydroxybutyric acid and S-beta-hydroxybutyric acid), a non-racemic mixture enriched with the R-enantiomer, or a non-racemic mixture enriched with the S-enantiomer. In some embodiments it is advantageous to include at least some amount of S-beta-hydroxybutyric acid in addition to or instead of R-beta-hydroxybutyric acid.

In a first embodiment, beta-hydroxybutyric acid compositions contain a non-racemic mixture enriched with the R-enantiomer, such as greater than 50% and less than 100% by enantiomeric equivalents of exogenous R-beta-hydroxybutyric acid and less than 50% and greater than 0% by enantiomeric equivalents of exogenous S-beta-hydroxybutyric acid.

In a second embodiment, beta-hydroxybutyric acid compositions contain a non-racemic mixture enriched with the S-enantiomer, such as greater than 50% and less than 100% by enantiomeric equivalents of exogenous S-beta-hydroxybutyric acid and less than 50% and greater than 0% by enantiomeric equivalents of exogenous R-beta-hydroxybutyric acid.

In a third embodiment, beta-hydroxybutyric acid compositions contain a racemic mixture of R-beta-hydroxybutyric acid and S-beta-hydroxybutyric acid, i.e., that contains 50% by enantiomeric equivalents of exogenous R-beta-hydroxybutyric acid and 50% by enantiomeric equivalents of exogenous S-beta-hydroxybutyric acid.

In a fourth embodiment, beta-hydroxybutyric acid compositions contain enantiomerically pure S-beta-hydroxybutyric acid, i.e., that contains 100% by enantiomeric equivalents of exogenous S-beta-hydroxybutyric acid and 0% by enantiomeric equivalents of R-beta-hydroxybutyric acid.

In a fifth embodiment, beta-hydroxybutyric acid compositions contain enantiomerically pure R-beta-hydroxybutyric acid, i.e., that contains 100% by enantiomeric equivalents of exogenous R-beta-hydroxybutyric acid and 0% by enantiomeric equivalents of S-beta-hydroxybutyric acid.

It is generally understood that only enantiomerically pure R-beta-hydroxybutyric acid and/or R-beta-hydroxybutyrate is produced endogenously and naturally by mammals so as to be a natural product. At biological pH, the endogenous form of beta-hydroxybutyric acid only exists as substantially deprotonated R-beta-hydroxybutyrate anions and not as a powder, solid, concentrated solution, or even dilute R-beta-hydroxybutyric acid solution within the disclosed concentrations.

S-beta-hydroxybutyric acid (S-beta-hydroxybutyrate at biological pH), which is not endogenously produced by mammals and is believed by some to be unnatural and potentially harmful, can provide other beneficial effects. These include one or more of: increased endogenous production of R-beta-hydroxybutyrate and acetoacetate; endogenous conversion into one or both of R-beta-hydroxybutyrate and acetoacetate; endogenous conversion into fatty acids and sterols; prolonged ketosis; metabolism of S-beta-hydroxybutyrate independent of its conversion to R-beta-hydroxybutyrate and/or acetoacetate; improved fetal development; increased growth years; reduced endogenous production of acetone during ketosis; signaling to modulate metabolism of R-beta-hydroxybutyrate and glucose; antioxidant activity; and production of acetyl-CoA.

Beta-hydroxybutyric acid compositions that are enriched with, or contain enantiomerically pure, S-beta-hydroxybutyric acid may be administered in higher doses than compositions enriched with, or that contain enantiomerically pure, R-beta-hydroxybutyric acid to obtain the same rapid supply of R-beta-hydroxybutyrate in the body. In such cases, it may be desirable to include incrementally higher, but still small, amounts of beta-hydroxybutyrate salts, such as less than 4%, 3%, or 2% of such salts by combined weight of beta-hydroxybutyric acid and beta-hydroxybutyrate salt(s), in order to further offset the acidity of beta-hydroxybutyric acid.

Beta-hydroxybutyric acid compositions disclosed herein may function to induce and/or sustain ketosis in a subject to which the composition is administered without significantly affecting electrolyte balance. This removes an otherwise limiting factor as to how much beta-hydroxybutyrate can be administered when administered in salt form. In addition, beta-hydroxybutyrate esters, particularly by themselves or when the primary source of beta-hydroxybutyrate, have an unpleasant taste and are not always well tolerated.

Beta-hydroxybutyric acid compositions can be useful as a weight loss supplement, as treatment for high blood glucose or type II diabetes, as brain tonic, as athletic performance enhancer, as preventative against metabolic dysfunction, mitochondrial defect, insulin resistance, as adjunct to a ketogenic diet, as anti-aging supplement, and for other uses associated with improved metabolic health.

Beta-hydroxybutyric acid compositions can be used in a method for increasing ketone body level in a subject in need thereof, including promoting and/or sustaining ketosis in the subject, comprising administering to the subject a nutritionally or pharmaceutically effective amount of beta-hydroxybutyric acid. Benefits of increased ketone body level in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

Additional features and advantages will be set forth in part in the description that follows, and in part will be obvious from the description, or may be learned by practice of the embodiments disclosed herein. It is to be understood that both the foregoing brief summary and the following detailed description are exemplary and explanatory only and are not restrictive of the embodiments disclosed herein or as claimed.

DETAILED DESCRIPTION

I. Introduction

Disclosed herein are beta-hydroxybutyric acid compositions for oral delivery and methods for their delivery, such as to increase ketone body level in a subject, including to promote and/or sustain ketosis in a subject while not affecting electrolytic balance and without causing acute acidosis or gastrointestinal (GI) distress. The beta-hydroxybutyric acid compositions are typically administered as an aqueous composition, suspension, or gel. Powder or solid beta-hydroxybutyric acid can be mixed with water, aqueous liquid, other liquid, gel, or food to form a solution containing beta-hydroxybutyric acid as a solute or a suspension containing beta-hydroxybutyric acid particles.

"Ketosis" refers to a subject having blood ketone levels within the range of about 0.5 mmol/L and about 16 mmol/L. Ketosis may improve mitochondrial function, decrease reactive oxygen species production, reduce inflammation, and increase the activity of neurotrophic factors. "Keto-adaptation" as used herein refers to prolonged nutritional ketosis (>1 week) to achieve a sustained nonpathological "mild ketosis" or "therapeutic ketosis."

In some cases, "elevated ketone body level" may not mean that a subject is in a state of "clinical ketosis" but nevertheless has an elevated supply of ketones for producing energy and/or for carrying out other beneficial effects of ketone bodies. For example, a subject that is "ketone adapted" may not necessarily have elevated blood serum levels of ketone bodies but rather is able to utilize available ketone bodies more rapidly compared to a subject that is not "ketone adapted." In such case, "elevated ketone body level" can refer to the total quantity and/or rate of ketone bodies being utilized by the subject rather than blood plasma levels per se.

"Exogenous ketone body" refers to beta-hydroxybutyrate and acetoacetate compounds that are not produced by a mammal. These compounds may be utilized by a subject's body as an energy source during instances of low glucose levels or when these compounds are supplemented in a usable form.

"Beta-hydroxybutyric acid" refers to exogenous beta-hydroxybutyric acid that can be in the form of a powder, other solid, solid particles in a suspension (e.g., sauce or gel), or solute in a solution, such as an aqueous solution.

"Aqueous beta-hydroxybutyric acid" refers to beta-hydroxybutyric acid dissolved in water or other aqueous liquid, in powder or other solid form, or in a gel or other suspension. Beta-hydroxybutyric acid that has self-polymerized to form an insoluble precipitate is not "aqueous beta-hydroxybutyric acid", although one will appreciate that aqueous beta-hydroxybutyric acid compositions may contain insoluble precipitates without causing harm.

A "suspension" means a liquid, syrup, gel, or other non-rigid composition with insufficient water to fully dissolve the beta-hydroxybutyric acid, at least a portion of which remains as undissolved particles surrounded by the suspending liquid, syrup, gel, or other non-rigid composition or carrier. Non-limiting examples of suspending agents include gels, foods, sauces, syrups, oils, and the like.

A "gel" refers to a composition that includes a gelling agent, such as a hydrocolloid, and a carrier, such as water or aqueous mixture. Gels can be in the form of a thick liquid, such as a viscous Newtonian fluid, or in the form of a Bingham plastic that does not flow under the force of gravity but can be deformed by applying pressure or other force.

Beta-hydroxybutyric acid compositions may be enriched with or contain enantiomerically pure R-beta-hydroxybutyric acid, enriched with or contain enantiomerically pure S-beta-hydroxybutyric acid, or be provided as a racemic mixture of R- and S-enantiomers. Beta-hydroxybutyric acid compositions, specifically those containing a racemic mixture or that are enriched with or contain enantiomerically pure, R-beta-hydroxybutyric acid, are free or substantially free of beta-hydroxybutyrate salts. Beta-hydroxybutyric acid compositions containing more S-beta-hydroxybutyric acid than R-beta-hydroxybutyric acid may be buffered with higher amounts of beta-hydroxybutyrate salt(s) when mixed with water.

Beta-hydroxybutyric acid compositions may optionally include acetoacetic acid, ester forms of beta-hydroxybutyrate and/or acetoacetate, ketone body precursors such as 1,3-butanediol or ester thereof.

Beta-hydroxybutyrate is the deprotonated form of beta-hydroxybutyric acid having the formula $CH_3CH_2OHCH_2COOH$. The deprotonated form present at typical biological pH levels is $CH_3CH_2OHCH_2COO^-$. The general chemical structure of beta-hydroxybutyrate is:

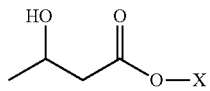

where, X can be hydrogen, metal ion, amino cation such as from an amino acid, alkyl, alkenyl, aryl, or acyl.

When X is a hydrogen, the compound is beta-hydroxybutyric acid. When X is a metal ion or an amino cation, the compounds is a beta-hydroxybutyrate salt. When X is alkyl, alkenyl, aryl, or acyl, the compounds is a beta-hydroxybutyrate ester. The foregoing compounds can be in any desired physical form, such as crystalline, powder, solid, liquid, solution, suspension, or gel.

Acetoacetate is the deprotonated form of acetoacetic acid having the formula $CH_3COCH_2COOH$. The deprotonated form present at typical biological pH levels is $CH_3COCH_2COO^-$. The general chemical structure of acetoacetate is:

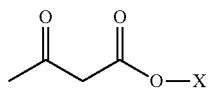

where, X can be hydrogen, metal ion, amino cation such as from an amino acid, alkyl, alkenyl, aryl, or acyl.

When X is a hydrogen, the compound is acetoacetic acid. When X is a metal ion or an amino cation, the compounds is an acetoacetate salt. When X is alkyl, alkenyl, aryl, or acyl, the compounds is an acetoacetate ester. The foregoing compounds can be in any desired physical form, such as crystalline, powder, solid, liquid, solution, suspension, or gel.

Unless otherwise specified, the term "salt" does not mean or imply any particular physical state, such as a crystalline, powder, other solid form, dissolved in water to form a liquid solution, dispersed in a liquid to form a suspension, or gel. A salt can be formed in solution, such as by at least partially neutralizing beta-hydroxybutyric acid with a strong or weak base, such as an alkali or alkaline earth metal hydroxide, carbonate, or bicarbonate, basic amino acid, and the like.

As used herein, "subject" or "patient" refers to members of the animal kingdom, including mammals, such as but not limited to, humans and other primates; rodents, fish, reptiles, and birds. The subject may be any animal requiring therapy, treatment, or prophylaxis, or any animal suspected of requiring therapy, treatment, or prophylaxis. Prophylaxis means that regiment is undertaken to prevent a possible occurrence, such as where a high glucose or diabetes is identified. "Patient" and "subject" are used interchangeably herein.

Beta-hydroxybutyric acid compositions can include enantiomerically pure R-beta-hydroxybutyric acid, enantiomerically pure S-beta-hydroxybutyric acid, a non-racemic mixture enriched with R-beta-hydroxybutyric acid relative to S-beta-hydroxybutyric acid, a non-racemic mixture enriched with S-beta-hydroxybutyric acid relative to R-beta-hydroxybutyric acid, or a racemic mixture of R- and S-beta-hydroxybutyric acids.

Whether the beta-hydroxybutyrate free acid, salt, or ester is the R- or S-enantiomer depends on the tetrahedral orientation of the hydroxy on the 3-carbon (beta-carbon) in relationship to the planar carboxyl group. R-beta-hydroxybutyrate is the endogenous form of beta-hydroxybutyric acid and can be utilized by a patient's body as a fuel source during instances of low glucose levels in the subject or when a patient's body is supplemented with a usable form of beta-hydroxybutyrate. S-beta-hydroxybutyrate is not endogenously produced by mammals but can promote one or more of: increased endogenous production of R-beta-hydroxybutyrate and acetoacetate; endogenous conversion into one or both of R-beta-hydroxybutyrate and acetoacetate; endogenous conversion into fatty acids and sterols; prolonged ketosis; direct metabolism of S-beta-hydroxybutyrate; improved fetal development; increased growth years; reduced endogenous production of acetone during ketosis; signaling to modulate metabolism of R-beta-hydroxybutyrate and glucose; antioxidant activity; and production of acetyl-CoA.

The term "unit dose" refers to a dosage form that is configured to orally deliver a specified quantity or dose of beta-hydroxybutyric acid. Example dosage forms of beta-hydroxybutyric acid include, but are not limited to, drinks (such as flavored, vitamin fortified, alcoholic, or non-alcoholic) in premeasured form, such as a can, bottle, carton, jug, and the like, drink additives, liquid energy shots, energy gel packs, foods, food additives, dietetically acceptable sprays (such as flavored mouth spray), and premeasured quantity of powder, solid, or gel, such as packets, pouches, tablets, capsules, effervescent tablets, and the like. Such dosage forms may be configured to provide a full unit dose or fraction thereof (e.g., ½, ⅓, or ¼ of a unit dose).

Another dosage form that can be used to provide a unit dose of beta-hydroxybutyric acid is a unit dose measuring device, such as a cup, scoop, syringe, dropper, spoon, spatula, or ladle, which is configured to hold therein a measured quantity of composition equaling a full unit dose or fraction thereof (e.g., ½, ⅓, or ¼ of a unit dose). For example, a bulk container, such as a carton, box, can, jar, bag, pouch, bottle, jug, or keg, containing several unit doses of composition (e.g., 5-250 or 10-150 unit doses) can be provided to a user together with a unit dose measuring device that is configured to provide a unit dose, or fraction thereof, of composition or component thereof.

A kit for use in providing beta-hydroxybutyric acid as disclosed herein in bulk form, while providing unit doses of the composition, may comprise a bulk container holding therein a quantity of composition and a unit dose measuring device configured to provide a unit dose, or fraction thereof, of composition or component thereof. One or more unit dose measuring devices may be positioned inside the bulk container at the time of sale, attached to the outside of the bulk container, prepackaged with the bulk container within a larger package, or provided by the seller or manufacture for use with one or multiple bulk containers. A bulk container may contain liquid or solid forms of beta-hydroxybutyric acid.

The kit may include instructions regarding the size of the unit dose, or fraction thereof, and the manner and frequency of administration. The instructions may be provided on the bulk container, prepackaged with the bulk container, placed on packaging material sold with the bulk container, or otherwise provided by the seller or manufacturer (e.g., on websites, mailers, flyers, product literature, etc.) The instructions for use may include a reference on how to use the unit dose measuring device to properly deliver a unit dose or fraction thereof. The instructions may additionally or alternatively include a reference to common unit dose measuring devices, such as cups, scoops, syringes, droppers, spoons, spatulas, ladles, and the like, not provided with the bulk container (e.g., in case the provided unit dose measuring device is lost or misplaced). In such case, a kit may be constructed by the end user when following instructions provided on or with the bulk container, or otherwise provided by the seller regarding the product and how to properly deliver a unit dose of composition, or fraction thereof.

In one embodiment, the container includes a quantity of tablets or capsules, such as effervescent tablets, each of which includes a premeasured quantity of beta-hydroxybutyric acid as a full or fractional dose. Capsules or tablets may further be grouped or contained within individual packets or pouches within the storage container, each containing a plurality of tablets or capsules that provide a pre-measured dosage of beta-hydroxybutyric acid.

The term "administration" or "administering" is used herein to describe the process in which the aqueous beta-hydroxybutyric acid compositions are orally delivered to a subject.

In some embodiments, the aqueous beta-hydroxybutyric acid compositions may be combined with a nutritionally or pharmaceutically acceptable carrier or additive.

II. Beta-Hydroxybutyric Acid Compositions

Administration of beta-hydroxybutyric acid in the form of an aqueous solution, readily digestible gel or suspension, provides a source of readily usable ketone bodies for producing metabolic energy. This is true regardless of whether the user is technically in state of ketosis. The body is able to metabolize both glucose and ketone bodies when present. If a sufficient quantity of beta-hydroxybutyric acid is consumed in a given time period, it can result in elevated and/or sustained blood levels of ketone bodies, thereby exploiting the metabolic and physiological advantages of ketosis without introducing a significant quantity of electrolytes into the blood. Raising ketone body level in the blood using exogenous ketones provides a subject with greater flexibility in diet options as compared to a method that aims to induce and sustain ketosis based on diet alone (e.g., based on fasting and/or limited carbohydrate intake). A subject that consumes an appropriate amount of beta-hydroxybutyric acid can eat an occasional carbohydrate or sugar-based food without jeopardizing the ketogenic state and shifting back into a glucose-based metabolic state. Further, administration of exogenous beta-hydroxybutyric acid facilitates easier transition to a ketogenic state while reducing or eliminating detrimental effects typically associated with entering ketosis.

Subjects entering or maintaining a ketogenic state may already be in a state of electrolyte imbalance due to metabolic shifts involved with ketosis, including enhanced diuretic effects and changes in insulin profiles. Thus, while there are many benefits to the administration of beta-hydroxybutyrate to promote or sustain ketosis in a subject, the resulting electrolyte imbalance when administering an excessive quantity and/or imbalanced ratio of salts and its associated detrimental physiological effects can offset the benefits of ketosis and/or make it more difficult for a subject to maintain ketosis at the desired levels or for a desired length of time.

For example, a formulation containing high levels and/or proportions of sodium beta-hydroxybutyrate can sharply increase sodium level in the subject. Excessive sodium can have detrimental effects, such as hypertension and poor cardiovascular health. High levels of sodium relative to potassium promotes hypertension and increases the risk of cardiovascular disease. A formulation containing high levels and/or proportions of calcium beta-hydroxybutyrate can sharply increase calcium level in the subject. Excessive calcium can build up in soft tissues, leading to detrimental calcification and hardening of such tissues and raising the risk of heart disease (e.g., associated with hardened arteries), kidney stones, arthritis, and other problematic conditions.

Aqueous beta-hydroxybutyric acid solutions, gels, and readily digestible suspensions provide a therapeutically effective amount of beta-hydroxybutyrate in the acid, and therefore most readily available form, without contributing significant or any salts. Such compositions provide the advantages of promoting, initiating, and/or sustaining ketosis without significantly altering electrolyte balance in the user, and in some cases even improving or easing electrolyte imbalances.

In general, aqueous beta-hydroxybutyric acid compositions for oral delivery that are free or substantially free of beta-hydroxybutyrate salts are effective in rapidly raising blood ketone levels without causing acute acidosis or gastrointestinal (GI) distress when consumed in sufficiently dilute form. In the absence of significant quantities of beta-hydroxybutyrate salts containing alkali or alkaline earth metal ions, aqueous beta-hydroxybutyric acid solutions can deliver exogenous ketone bodies without significantly altering electrolyte balance. By providing aqueous beta-hydroxybutyric acid at a concentration within specific ranges, it is possible to maintain beta-hydroxybutyric acid stability and prevent self-esterification and precipitation.

In some embodiments, aqueous beta-hydroxybutyric acid solutions can have a concentration that is sufficiently diluted such that volumes in a range of about 4 oz. (about 120 ml) to about 16 oz. (about 475 ml) can deliver a quantity of ketone bodies in a range of about 0.5 gram to about 25 grams, without harming the stomach or causing significant acidosis. For example, dilute aqueous beta-hydroxybutyric acid solutions can have a concentration of beta-hydroxybutyric acid in a range of about 0.4% w/v to about 6% w/v, or about 0.6% w/v to about 5.5% w/v, or about 0.9% w/v to about 5% w/v, or about 1.2% w/v to about 4.5% w/v, or about 1.5% w/v to about 4% w/v. Although aqueous beta-hydroxybutyric acid solutions are moderately acidic, with a pH of about 3.5 to 4, when diluted with sufficient water, the water itself acts as a pseudo buffering agent that offsets the otherwise harsh effects of the acid when consumed orally.

In some embodiments, aqueous beta-hydroxybutyric acid solutions can be provided as a concentrate for later dilution by the user, such as with water, juice, drink, energy shot, or other aqueous composition to a concentration in a range of about 0.4% w/v to about 6% w/v, or about 0.6% w/v to about 5.5% w/v, or about 0.9% w/v to about 5% w/v, or about 1.2% w/v to about 4.5% w/v, or about 1.5% w/v to about 4% w/v. Concentrated solutions may comprise beta-hydroxybutyric acid in a range of about 6% w/v to about 60% w/v, or about 8% w/v to about 55% w/v, or about 10% w/v to about 50% w/v, or about 12.5% w/v to about 45% w/v, or about 15% w/v to about 40% w/v, and then diluted by the user as desired, such as from about 2 to about 30 times, or about 3 to about 25 times, or about 4 to about 2 times, or about 5 to about 15 times, with water, juice, drink, or other aqueous composition, as desired. Preferably, the aqueous beta-hydroxybutyric acid solutions will not be so concentrated that they will self-polymerize and form significant amounts of precipitates, although it should be understood that such polymerized precipitates are harmless and some may be re-hydrolyzed in acidic solutions, perhaps under certain conditions in the stomach when consumed with sufficient water.

Beta-hydroxybutyric acid compositions are free or substantially free of beta-hydroxybutyrate salts so as to contain less than 1%, or less than 0.9%, or less than 0.8%, or less than 0.7%, or less than 0.6%, or less than 0.5%, or less than 0.4%, or less than 0.3%, or less than 0.2%, or less than 0.1% of one or more beta-hydroxybutyrate salts by combined weight of beta-hydroxybutyric acid and beta-hydroxybutyrate salt(s). Beta-hydroxybutyric acid compositions can be essentially or totally free of beta-hydroxybutyrate salts, i.e., contain 0% by weight of beta-hydroxybutyrate salts.

In some embodiments, beta-hydroxybutyric acid compositions may contain one or more nutritionally or pharmaceutically acceptable carriers or additives. For example, beta-hydroxybutyric acid compositions may optionally include at least one additive selected from acetoacetic acid, ethanol, glycerin, propylene glycol, 1,3-butanediol, gelling agents (e.g., gellan gum, pectin, agar, carrageenan, xanthan gum, alginate, starch, modified starch, gum Arabic, guar gum, locust bean gum, konjac maanan, gum tragacanth, acacia gum, gum karaya, methyl cellulose, agar, pullulan, konjac, hydroxypropylmethyl cellulose, other cellulosic compounds, other polysaccharide gums, gelatin, collagen, casein, other proteins, silica fume, milled chia seeds, and other hydrocolloids), effervescing agents (e.g., edible acid and bicarbonate or carbonate compound), beta-hydroxybutyrate esters, vitamins, minerals, central nervous system stimulants, nootropics, edible acids, amino acids, muscle-promoting compounds, (e.g., beta-hydroxy beta-methylbutyrate (HMB)), one or more cannabinoids (e.g., tetrahydrocannabinol and/or cannabidiol), and the like. The beta-hydroxybutyric acid composition may include flavoring agents, such as essential oils, e.g., peppermint, spearmint, wintergreen, or citrus oils, natural and artificial sweeteners, and other flavorants known in the art.

In some embodiments, concentrated or dilute beta-hydroxybutyric acid solutions, gels, sauces, and other compositions can be manufactured by combining a powder or other solid form of beta-hydroxybutyric acid with water, drink, beverage, sauce, gel, or other liquid or semi-liquid drink or food product. When the beta-hydroxybutyric acid solution is prepared by a user, the powder or other solid form of beta-hydroxybutyric acid will advantageously include a flavoring agent and may contain other additives, such as one or more of stabilizer (e.g., edible acids, silica, starch, and the like), effervescing agents (e.g., bicarbonate, carbonate, and optionally another acid), vitamin, mineral, stimulant, nootropic, vasodilator, cannabinoid, amino acid, and the like.

The powder, other solid, or gel may be provided in individual pre-dosed packets, pouches, tablets, or capsules, or it may be provided in a kit with a measuring device configured to measure out a predetermined dose or fraction thereof. A plurality (e.g., 2 or 3) of dissolvable tablets representing a single dose can be packaged together in a packet, pouch, or other container. In some embodiments, a dissolvable tablet may be effervescent and fizz when added to water. In the case of an effervescent tablet, it may be desirable to include a quantity of an edible acid (e.g., citric, malic, fumaric, lactic, tartaric, malonic, succinic, adipic, folic, or butyric) together with a bicarbonate salt to provide the desired effervescent action yet provide less than 1% of total beta-hydroxybutyrate salt(s) upon dissolution in water (i.e., if the edible acid has a lower pKa than beta-hydroxybutyric acid a salt of the edible acid will form preferentially over beta-hydroxybutyrate salt).

In various embodiments, beta-hydroxybutyric acid compositions may include enantiomerically pure R-beta-hydroxybutyric acid, a racemic mixture of R- and S-beta-hydroxybutyric acid (i.e., a mixture having a 1:1 ratio of R-beta-hydroxybutyric acid and S-beta-hydroxybutyric acid enantiomers), a non-racemic mixture enriched with the R-enantiomer, or a non-racemic mixture enriched with the S-enantiomer. In some embodiments it is advantageous to include at least some amount of S-beta-hydroxybutyric acid in addition to or instead of R-beta-hydroxybutyric acid.

In a first embodiment, beta-hydroxybutyric acid compositions contain a non-racemic mixture enriched with the R-enantiomer, such as greater than 50% and less than 100% by enantiomeric equivalents of exogenous R-beta-hydroxybutyric acid and less than 50% and greater than 0% by enantiomeric equivalents of exogenous S-beta-hydroxybutyric acid. In some embodiments, a non-racemic mixture of R- and S-beta-hydroxybutyric acid forms contain 50.1% to 99.9%, 50.2% to 99.8%, 50.3% to 99.7%, 50.4% to 99.6%, 50.5% to 99.5%, 51% to 99%, 52% to 98%, 53% to 97%, 54% to 96%, 55% to 95%, 57% to 93%, or 60% to 90% by enantiomeric equivalents of R-beta-hydroxybutyric acid and 49.9% to 0.1%, 49.8% to 0.2%, 49.7% to 0.3%, 49.6% to 0.4%, 49.5% to 0.5%, 49% to 1%, 48% to 2%, 47% to 3%, 46% to 4%, 45% to 5%, 43% to 7%, 41% to 15%, or 40% to 10% by enantiomeric equivalents of S-beta-hydroxybutyric acid.

In a second embodiment, beta-hydroxybutyric acid compositions contain a non-racemic mixture enriched with the S-enantiomer, such as greater than 50% and less than 100% by enantiomeric equivalents of exogenous S-beta-hydroxybutyric acid and less than 50% and greater than 0% by enantiomeric equivalents of exogenous R-beta-hydroxybutyric acid. In some embodiments, a non-racemic mixture of S- and R-beta-hydroxybutyric acid forms contain 50.1% to 99.9%, 50.2% to 99.8%, 50.3% to 99.7%, 50.4% to 99.6%, 50.5% to 99.5%, 51% to 99%, 52% to 98%, 53% to 97%, 54% to 96%, 55% to 95%, 57% to 93%, or 60% to 90% by enantiomeric equivalents of S-beta-hydroxybutyric acid and 49.9% to 0.1%, 49.8% to 0.2%, 49.7% to 0.3%, 49.6% to 0.4%, 49.5% to 0.5%, 49% to 1%, 48% to 2%, 47% to 3%, 46% to 4%, 45% to 5%, 43% to 7%, 41% to 15%, or 40% to 10% by enantiomeric equivalents of R-beta-hydroxybutyric acid.

In a third embodiment, beta-hydroxybutyric acid compositions contain a racemic (or near racemic) mixture of R-beta-hydroxybutyric acid and S-beta-hydroxybutyric acid, i.e., that contains 50% by enantiomeric equivalents of exogenous R-beta-hydroxybutyric acid and 50% by enantiomeric equivalents of exogenous S-beta-hydroxybutyric acid. A near racemic mixture that is not a perfect 50:50 mixture of R- and S-enantiomers may include about 49.9% to about 50.1%, or about 49.92% to about 50.08%, or about 49.94% to about 50.06%, or about 49.96% to about 50.04%, or about 49.98% to about 50.02%, by enantiomeric equivalents of R-beta-hydroxybutyrate and about 50.1% to about 49.9%, or about 50.06% to about 49.94%, or about 50.04% to about 49.96%, or about 50.02% to about 49.98%, by enantiomeric equivalents of S-beta-hydroxybutyrate.

In a fourth embodiment, beta-hydroxybutyric acid compositions contain enantiomerically pure S-beta-hydroxybutyric acid, i.e., that contains 100% by enantiomeric equivalents of exogenous S-beta-hydroxybutyric acid and 0% by enantiomeric equivalents of R-beta-hydroxybutyric acid.

In a fifth embodiment, beta-hydroxybutyric acid compositions contain enantiomerically pure R-beta-hydroxybutyric acid, i.e., that contains 100% by enantiomeric equivalents of exogenous R-beta-hydroxybutyric acid and 0% by enantiomeric equivalents of S-beta-hydroxybutyric acid. Because exogenous R-beta-hydroxybutyric acid dissolved in water to form an aqueous solution with a "water buffer" is not found in nature, it is not a "natural product".

It is generally understood that only enantiomerically pure R-beta-hydroxybutyric acid and/or R-beta-hydroxybutyrate is produced endogenously and naturally by mammals so as to be a natural product. At biological pH, the endogenous form of beta-hydroxybutyric acid only exists as substantially deprotonated R-beta-hydroxybutyrate anions and not in powder or other solid form, concentrated solution, or even dilute aqueous R-beta-hydroxybutyric acid within the disclosed concentrations.

S-beta-hydroxybutyric acid (S-beta-hydroxybutyrate at biological pH), which is not endogenously produced by mammals and is believed by some to be unnatural and potentially harmful, can provide other beneficial effects. These include one or more of: increased endogenous production of R-beta-hydroxybutyrate and acetoacetate; endogenous conversion into one or both of R-beta-hydroxybutyrate and acetoacetate; endogenous conversion into fatty acids and sterols; prolonged ketosis; metabolism of S-beta-hydroxybutyrate independent of its conversion to R-beta-hydroxybutyrate and/or acetoacetate; improved fetal development; increased growth years; reduced endogenous production of acetone during ketosis; signaling to modulate metabolism of R-beta-hydroxybutyrate and glucose; antioxidant activity; and production of acetyl-CoA.

Beta-hydroxybutyric acid enriched with, or that contains enantiomerically pure, S-beta-hydroxybutyric acid may be administered in higher doses than compositions enriched with, or that contain enantiomerically pure, R-beta-hydroxybutyric acid to obtain the same rapid supply of R-beta-hydroxybutyrate in the body. In such cases, it may be desirable to include incrementally higher, but still small, amounts of beta-hydroxybutyrate salts, such as less than 4.0%, or less than 3.75%, or less than 3.5%, or less than 3.25%, or less than 3.0%, or less than 2.75%, or less than 2.5% or less than 2.25%, or less than 2%, or less than 1.75%, or less than 1.5%, or less than 1.25%, of such salts by combined weight of beta-hydroxybutyric acid and beta-hydroxybutyrate salt(s), in order to further offset the greater acidity of higher concentrations and/or amounts of beta-hydroxybutyric acid in compositions that are enriched with, or contain enantiomerically pure, S-beta-hydroxybutyric acid.

In some embodiments, beta-hydroxybutyric acid compositions may optionally include beta-hydroxybutyrate salts in which the cations are provided by an amino acid or other organic compound having a net positive charge at acidic pH. beta-hydroxybutyrate-amino acid compounds can provide a soluble form of beta-hydroxybutyrate without providing electrolytes such as sodium, potassium, calcium or magnesium. Most amino acids have a net positive charge at acidic pH. Examples include arginine, lysine, leucine, iso-leucine, histidine, ornithine, citrulline, glutamine, or other suitable amino acids or metabolites of amino acids (e.g., creatine). Some amino acids also provide health benefits. For example, arginine and citrulline can increase nitric oxide in the blood, which dilates blood vessels and improves blood circulation for persons with heart conditions (and may help men suffering from erectile dysfunction).

In some embodiments, beta-hydroxybutyric acid compositions can be provided as an aqueous solution, such as in the form of a beverage, a concentrated energy shot, or mouth spray for fast delivery and absorption. Beta-hydroxybutyric acid compositions can be provided as gel, such as an energy gel. Beta-hydroxybutyric acid compositions can be provided as a food product, such as a sauce or condiment. Beta-hydroxybutyric acid compositions can be provided as a powder or other solid that can be added to water, drink or food to form an ingestible aqueous solution, gel or suspension.

In addition to water, beta-hydroxybutyric acid compositions may optionally include other liquid carriers, such as water, ethanol, glycerin, propylene glycol, 1,3-propandiol, and the like. The compositions may include vitamins and/or minerals. Other additives include metabolites that enhance the effect or transport of ketone bodies into mitochondria, caffeine, theobromine, and nootropics, such as L-alpha glycerylphosphorylcholine ("alpha GPC"). The compositions may include flavoring agents, such as essential oils, e.g., peppermint, spearmint, wintergreen, or citrus oils, natural and artificial sweeteners, and other flavorants known in the art.

Beta-hydroxybutyric acid compositions can optionally include one or more beta-hydroxybutyrate esters. Example beta-hydroxybutyrate esters include mono-, di-, tri-, oligo-, and polyesters. Examples include mono-ester of ethanol, mono-ester of 1-propanol, mono-ester of 1,2-propanediol, di-ester of 1,2-propanediol, mono-ester of 1,3-propanediol, di-ester of 1,3-propanediol, mono- or di-ester of S-, R-, or S—R-1,3-butanediol, mono-, di-, or tri-ester of glycerin, ester of acetoacetate, dimers, trimers, oligomers, and polyesters containing repeating units of beta-hydroxybutyrate, and complex oligomers or polymers of beta-hydroxybutyrate and one or more other hydroxy-carboxylic acids, such as lactic acid, citric acid, acetoacetic acid, quinic acid, shikimic acid, salicylic acid, tartaric acid, and malic acid, and/or beta-hydroxybutyrate and or one or more diols, such as 1,3-propanediol and 1,3-butanediol, and one or more polyacids, such as tartaric acid, citric acid, malic acid, succinic acid, and fumaric acid.

Beta-hydroxybutyric acid compositions may optionally include short-, medium-, and/or long-chain fatty acids and/or esters thereof. Most of such components can have limited solubility in water and may require use of emulsifier and/or remain as particles in suspension, while water soluble forms, particularly short chain fatty acids, have a very strong taste. Short chain fatty acids contain 2 to 5 carbon atoms and include acetic acid, propionic acid, butyric acid, isobutyric acid, valeric acid, and isovaleric acid. Medium chain fatty acids contain from 6 to 12 carbons and include caproic acid, caprylic acid, capric acid, and lauric acid. Long chain fatty acids contain more than 12 carbon atoms and include myristic acid, palmitic acid, stearic acid, arachidic acid, behenic acid, lignoceric acid, cerotic acid, omega-3 fatty acids, omega-6 fatty acids, omega-7 fatty acids, and omega-9 fatty acids. In preferred embodiments, aqueous beta-hydroxybutyric acid compositions are substantially free of short-, medium-, and long-chain fatty acids and esters thereof, such as less than 5%, 4%, 3%, 2%, or 1%.

III. Administration

Beta-hydroxybutyric acid compositions can be used in a method for increasing ketone body level, including promoting and/or sustaining ketosis, in a subject comprising administering to a subject in need thereof a nutritionally or pharmaceutically effective amount of beta-hydroxybutyric acid. Examples of beneficial effects of increasing ketone body level, including promoting and/or sustaining ketosis, in a subject include one or more of appetite suppression, weight loss, fat loss, reduced blood glucose level, improved mental alertness, increased physical energy, improved cognitive function, reduction in traumatic brain injury, reduction in effect of diabetes, improvement of neurological disorder, reduction of cancer, reduction of inflammation, anti-aging, antiglycation, reduction in epileptic seizer, improved mood, increased strength, increased muscle mass, or improved body composition.

Beta-hydroxybutyric acid can be administered to a subject in therapeutically effective dosages and/or in frequencies to induce or sustain ketosis. In some embodiments, a single dose may provide from about 0.5 gram to about 25 grams, or about 0.75 gram to about 20 grams, or about 1 gram to about 15 grams, or about 1.5 grams to about 12 grams, or about 2 grams to about 10 grams of combined weight of beta-hydroxybutyric acid and beta-hydroxybutyrate compounds.

Beta-hydroxybutyric acid compositions can include or be administered together with other supplements, such as vitamin D3, vitamins, minerals, nootropics, and others known in the art. Examples of vitamins, minerals and herbal supplements that can be added to the ketogenic compositions include one or more of vitamin A, vitamin C, vitamin E, niacin, vitamin B6, folic acid, 5-MTHF, vitamin B12, iodine, zinc, copper, manganese, chromium, caffeine, theobromine, theacrine, methylliberine, huperzine A, epicatechins, and enzymes.

In some embodiments, the subject may follow a ketogenic diet that restricts intake of carbohydrates and protein during the period of administration. In one example embodiment, the subject may restrict the dietary intake to a ratio of about 65% fat, about 25% protein, and about 10% carbohydrates. The resulting therapeutic ketosis provides a rapid and sustained keto-adaptation as a metabolic therapy for a wide range of metabolic disorders, and provides nutritional support for therapeutic fasting, weight loss, and performance enhancement. As such, the composition is typically administered once per day, twice per day, or three times per day to a subject desiring to promote and/or sustain a state of ketosis.

In some embodiments, multiple doses of the composition are administered over time. The frequency of administration of the composition can vary depending on any of a variety of factors, such as timing of treatment from previous treatments, objectives of the treatment, and the like. The duration of administration of the composition (e.g., the time period over which the agent is administered), can vary depending on any of a variety of factors, including subject response, desired effect of treatment, etc.

The amount of the composition to be administered can vary according to factors such as the degree of susceptibility of the individual, the age, sex, and weight of the individual, idiosyncratic responses of the individual, and the like. The "therapeutically effective amount" is that amount necessary to promote a therapeutically effective result in vivo (i.e., therapeutic ketosis). In accordance with the present disclosure, a suitable single dose size is a dose that is capable of preventing or alleviating (reducing or eliminating) a symptom in a patient when administered one or more times over a suitable time period.

The amount of composition administered will depend on potency, absorption, distribution, metabolism, and excretion rates of unused ketone bodies, electrolytes, the method of administration, and the particular disorder being treated, as well as other factors known to those of skill in the art. The dose should be sufficient to affect a desirable response, such as a therapeutic or prophylactic response against a particular disorder or condition, taking into account the severity of the condition to be alleviated. The aqueous beta-hydroxybutyric acid solution may be administered once, or may be divided and administered over intervals of time. It is to be understood that administration may be adjusted according to individual need and professional judgment of a person administrating or supervising the administration of the compositions.

IV. EXAMPLES

The following is a description of exemplary aqueous beta-hydroxybutyric acid solutions, gels, and suspensions, and solid compositions used to make such solutions, gels, or suspensions, useful for delivering ketone bodies to a subject in need thereof, including to induce and/or sustain a ketogenic state in a subject to which they are administered, without delivering a significant quantity of electrolytes.

Example 1

An aqueous beta-hydroxybutyric acid solution is prepared by mixing beta-hydroxybutyric acid (e.g., powder or other solid form) with water to form a highly concentrated solution containing 60% w/v of beta-hydroxybutyric acid. The concentrated aqueous beta-hydroxybutyric acid solution is readily administered as a ketogenic composition by mixing with 10 to 30 parts of water, juice, beverage, or other aqueous composition.

Example 2

An aqueous beta-hydroxybutyric acid solution is prepared by mixing beta-hydroxybutyric acid (e.g., powder or other solid form) with water to form a highly concentrated solution containing 50% w/v of beta-hydroxybutyric acid. The concentrated aqueous beta-hydroxybutyric acid solution is readily administered as a ketogenic composition by mixing with 9 to 28 parts of water, juice, beverage, or other aqueous composition.

Example 3

An aqueous beta-hydroxybutyric acid solution is prepared by mixing beta-hydroxybutyric acid (e.g., powder or other solid form or more concentrated solution) with water to form a less highly concentrated solution containing 40% w/v of beta-hydroxybutyric acid. The concentrated aqueous beta-hydroxybutyric acid solution is readily administered as a ketogenic composition by mixing with 8 to 25 parts of water, juice, beverage, or other aqueous composition.

Example 4

An aqueous beta-hydroxybutyric acid solution is prepared by mixing beta-hydroxybutyric acid (e.g., powder or other solid form or more concentrated solution) with water to form a less highly concentrated solution containing 35% w/v of beta-hydroxybutyric acid. The concentrated aqueous beta-hydroxybutyric acid solution is readily administered as a ketogenic composition by mixing with 7 to 22 parts of water, juice, beverage, or other aqueous composition.

Example 5

An aqueous beta-hydroxybutyric acid solution is prepared by mixing beta-hydroxybutyric acid (e.g., powder or other solid form or more concentrated solution) with water to form a moderately concentrated solution containing 30% w/v of beta-hydroxybutyric acid. The concentrated aqueous beta-hydroxybutyric acid solution is readily administered as a ketogenic composition by mixing with 6 to 18 parts of water, juice, beverage, or other aqueous composition.

Example 6

An aqueous beta-hydroxybutyric acid solution is prepared by mixing beta-hydroxybutyric acid (e.g., powder or other solid form or more concentrated solution) with water to form a moderately concentrated solution containing 25% w/v of beta-hydroxybutyric acid. The concentrated aqueous beta-hydroxybutyric acid solution is readily administered as a ketogenic composition by mixing with 5 to 15 parts of water, juice, beverage, or other aqueous composition.

Example 7

An aqueous beta-hydroxybutyric acid solution is prepared by mixing beta-hydroxybutyric acid (e.g., powder or other solid form or more concentrated solution) with water to form a moderately concentrated solution containing 20% w/v of beta-hydroxybutyric acid. The concentrated aqueous beta-hydroxybutyric acid solution is readily administered as a ketogenic composition by mixing with 4 to 12 parts of water, juice, beverage, or other aqueous composition.

Example 8

An aqueous beta-hydroxybutyric acid solution is prepared by mixing beta-hydroxybutyric acid (e.g., powder or other solid form or more concentrated solution) with water to form a fairly concentrated solution containing 15% w/v of beta-hydroxybutyric acid. The concentrated aqueous beta-hydroxybutyric acid solution is readily administered as a ketogenic composition by mixing with 3 to 9 parts of water, juice, beverage, or other aqueous composition.

Example 9

An aqueous beta-hydroxybutyric acid solution is prepared by mixing beta-hydroxybutyric acid (e.g., powder or other solid form or more concentrated solution) with water to form a fairly concentrated solution containing 10% w/v of beta-hydroxybutyric acid. The concentrated aqueous beta-hydroxybutyric acid solution is readily administered as a ketogenic composition by mixing with 2 to 8 parts of water, juice, beverage, or other aqueous composition.

Example 10

An aqueous beta-hydroxybutyric acid solution is prepared by mixing beta-hydroxybutyric acid (e.g., powder or other solid form or more concentrated solution) with water to form a fairly dilute solution containing 6% w/v of beta-hydroxybutyric acid. The aqueous beta-hydroxybutyric acid solution can be used as is or mixed with another substance.

Example 11

An aqueous beta-hydroxybutyric acid solution is prepared by mixing beta-hydroxybutyric acid (e.g., powder or other solid form or more concentrated solution) with water to form a fairly dilute solution containing 5% w/v of beta-hydroxybutyric acid. The aqueous beta-hydroxybutyric acid solution can be used as is or mixed with another substance.

Example 12

An aqueous beta-hydroxybutyric acid solution is prepared by mixing beta-hydroxybutyric acid (e.g., powder or other solid form or more concentrated solution) with water to form a moderately dilute solution containing 4% w/v of beta-hydroxybutyric acid. The aqueous beta-hydroxybutyric acid solution can be used as is or mixed with another substance.

Example 13

An aqueous beta-hydroxybutyric acid solution is prepared by mixing beta-hydroxybutyric acid (e.g., powder or other solid form or more concentrated solution) with water to form a more dilute solution containing 3% w/v of beta-hydroxybutyric acid. The aqueous beta-hydroxybutyric acid solution can be used as is or mixed with another substance.

Example 14

An aqueous beta-hydroxybutyric acid solution is prepared by mixing beta-hydroxybutyric acid (e.g., powder or other solid form or more concentrated solution) with water to form an even more dilute solution containing 2% w/v of beta-hydroxybutyric acid. The aqueous beta-hydroxybutyric acid solution can be used as is or mixed with another substance.

Example 15

An aqueous beta-hydroxybutyric acid solution is prepared by mixing beta-hydroxybutyric acid (e.g., powder or other solid form or more concentrated solution) with water to form a very dilute solution containing 1.5% w/v of beta-hydroxybutyric acid. The aqueous beta-hydroxybutyric acid solution can be used as is or mixed with another substance.

Example 16

An aqueous beta-hydroxybutyric acid solution is prepared by mixing beta-hydroxybutyric acid (e.g., powder or other solid form or more concentrated solution) with water to form a highly dilute solution containing 1% w/v of beta-hydroxybutyric acid. The aqueous beta-hydroxybutyric acid solution can be used as is or mixed with another substance.

Example 17

Any of the foregoing aqueous beta-hydroxybutyric acid solutions is modified by including a gelling agent to form a gel. The gelling agent can be one or more of gellan gum, pectin, agar, carrageenan, xanthan gum, alginate, starch, modified starch, gum Arabic, guar gum, locust bean gum, konjac maanan, gum tragacanth, acacia gum, gum karaya, methyl cellulose, agar, pullulan, konjac, hydroxypropylmethyl cellulose, other cellulosic compounds, other polysaccharide gums, gelatin, collagen, casein, other proteins, silica fume, milled chia seeds, and other hydrocolloids. The gelling agent is included in an amount to yield a gel of desired consistency, such as a viscous Newtonian fluid or a Bingham plastic.

Example 18

Any of the foregoing beta-hydroxybutyric acid solutions or gels include other carrier materials in which beta-hydroxybutyric acid is insoluble or less soluble in order to form a suspension containing particles of beta-hydroxybutyric acid. In some cases the quantity of water is reduced to be less than the amount required to dissolve the beta-hydroxybutyric acid. The suspension can be a liquid, a gel, a sauce, or other food or drink material.

Example 19

Any of the foregoing beta-hydroxybutyric acid compositions is combined with one or more short chain fatty acids or ester thereof.

Example 20

Any of the foregoing beta-hydroxybutyric acid compositions is combined with a beta-hydroxybutyrate compound containing a cationic amino acid selected from arginine, lysine, leucine, iso-leucine, histidine, ornithine, citrulline, L-glutamine, or metabolite of an amino acid, such as creatine). The beta-hydroxybutyrate amino acid compound provides an additional source of beta-hydroxybutyrate without adding electrolytes to the composition.

Example 21

Any of the foregoing beta-hydroxybutyric acid compositions can include a non-racemic mixture enriched with R-beta-hydroxybutyric acid, which can be prepared by mixing R-beta-hydroxybutyric acid with a racemic mixture of R- and S-beta-hydroxybutyric acids to provide greater than 50% and less than 100% by enantiomeric equivalents of R-beta-hydroxybutyric acid and less than 50% and greater than 0% by enantiomeric equivalents of S-beta-hydroxybutyric acid. Because the non-racemic mixture includes more of the R-enantiomer, the onset of ketosis is accelerated for a given dosage as compared to the same dosage of a racemic mixture. On the other hand, including the S-enantiomer provides for a longer state of ketosis and/or other benefits as disclosed herein compared to using pure R-beta-hydroxybutyric acid.

Example 22

Any of the foregoing beta-hydroxybutyric acid compositions can include a non-racemic mixture enriched with S-beta-hydroxybutyric acid, which can be prepared by mixing S-beta-hydroxybutyric acid with a racemic mixture of R- and S-beta-hydroxybutyric acids to provide greater than 50% and less than 100% by enantiomeric equivalents of S-beta-hydroxybutyric acid and less than 50% and greater than 0% by enantiomeric equivalents of R-beta-hydroxybutyric acid. Because the non-racemic mixture includes more of the S-enantiomer, the onset of ketosis is delayed for a given dosage as compared to the same dosage of a racemic mixture.

Example 23

Any of the foregoing beta-hydroxybutyric acid compositions can include a racemic mixture of R-beta-hydroxybutyric acid and S-beta-hydroxybutyric acid to provide 50% by enantiomeric equivalents of the R-enantiomer and 50% by enantiomeric equivalents of the S-enantiomer. Because the composition contains a racemic mixture, the onset of ketosis is accelerated for a given dosage as compared to the same dosage enriched with the S-enantiomer. On the other hand, because the racemic mixture includes 50% by enantiomeric equivalents of the S-enantiomer, the duration of sustained ketosis is increased for a given dosage as compared to the same dosage enriched with the R-enantiomer.

Example 24

Any of the foregoing beta-hydroxybutyric acid compositions is modified by including one or more supplements, such as one or more vitamins, minerals, herbs, and others known in the art.

Example 25

Any of the foregoing beta-hydroxybutyric acid compositions is modified by including one or more beta-hydroxybutyrate esters.

Example 26

Any of the foregoing beta-hydroxybutyric acid compositions is modified by including one or more fat burner supplements such as green tea, green tea extract (e.g., a composition including one or more isolated green tea catechins such as epigallocatechin gallate (EGCG)), green coffee extract, conjugated linoleic acid (CLA), tetradecyl thioacetic acid (TTA), *Coleus forskohlii* (i.e., forskolin), yohimbine, rauwolscine, capsaicin, raspberry ketones (e.g., 4-(4-hydroxyphenyl) butan-2-one, p-hydroxybenzyl acetone), ephedrine, synephrine (e.g., bitter orange extract), octopamine, 1,3-dimethylamylamine, higenamine, fucoxanthin, acetylcholine modulators and/or adenosine receptor antagonists (e.g., caffeine), nicotine, coca leaf derivative, ursolic acid, clenbuterol, noradrenaline reuptake inhibitors (e.g., hordenine, atomoxetine), 7-oxodehydroepiandrosterone (i.e., 7-keto DHEA), thyroid hormones (e.g., triiodothyronine), and combinations thereof. The resulting combined supplement is expected to provide greater lipolysis and/or fat oxidation effects than a similar dose that includes only beta-hydroxybutyrate compounds.

Example 27

Any of the foregoing beta-hydroxybutyric acid compositions is modified by including one or more nootropic supplements such as tyrosine, L-DOPA (i.e., L-3,4-dihydroxyphenylalanine), tryptophan, and 5-hydroxytryptophan (5-HTP), racetams such as such as piracetam, oxiracetam, and aniracetam, L-theanine, D-serine, phosphatidylserine, tolcapone, uridine, vinpocetine, norepinephrine reuptake inhibitors such as hordenine and atomoxetine, *Panax ginseng, Ginkgo biloba, Rhodiola rosea, Polygala tenuifolia, Muira puama, Eschscholzia californica, Convolvulus pluricaulis, Centella asiatica, Evolvulus alsinoides, Bacopa monnieri, Epimedium* herbs, *Ashwagandha* herbs, cyclic adenosine monophosphate (cAMP) modulators such as forskolin, stimulants such as nicotine, caffeine, and amphetamines, cholinergic compounds and/or acetylcholine modulators such as huperzine-A, dimethylaminoethanol, choline, and alpha-glycerophosphocholine, and combinations thereof. The resulting combined supplement is expected to provide greater cognition, alertness, and/or mood effects than a similar dose that includes only beta-hydroxybutyrate compounds.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. An aqueous beta-hydroxybutyric acid composition formulated as a nutritional supplement, or for addition to water, beverage, or food product, for ingestion by oral delivery to provide exogenous ketone bodies that exogenously increase blood ketone level in a mammal, the composition comprising:
   water; and
   0.4% w/v to 55% w/v of exogenous beta-hydroxybutyric acid in monomeric form at least partially dissolved in the water,
   wherein the composition is free or substantially free of beta-hydroxybutyrate salts so as to contain less than 0.8% of total beta-hydroxybutyrate salts and greater than 99.2% of the exogenous beta-hydroxybutyric acid by combined weight of the exogenous beta-hydroxybutyric acid and any beta-hydroxybutyrate salts,
   wherein the composition is free of 1,3-butanediol and ketone esters,
   wherein the composition is a nutritional supplement that provides a unit dose of about 0.5 gram to about 25 grams of the exogenous beta-hydroxybutyric acid to exogenously increase blood ketone level in a mammal.

2. The aqueous beta-hydroxybutyric acid composition of claim 1, wherein the composition is a dilute solution in which the exogenous beta-hydroxybutyric acid has a concentration of about 0.4% w/v to about 6% w/v.

3. The aqueous beta-hydroxybutyric acid composition of claim 2, wherein the exogenous beta-hydroxybutyric acid has a concentration of about 0.6% w/v to about 5.5% w/v, or about 0.9% w/v to about 5% w/v, or about 1.2% w/v to about 4.5% w/v, or about 1.5% w/v to about 4% w/v.

4. The aqueous beta-hydroxybutyric acid composition of claim 1, wherein about 4 oz. (about 120 ml) to about 16 oz. (about 475 ml) of the composition provides the unit dose of about 0.5 gram to about 25 grams of the exogenous beta-hydroxybutyrate to the mammal when consumed orally.

5. The aqueous beta-hydroxybutyric acid composition of claim 4, wherein about 4 oz. (about 120 ml) to about 16 oz. (about 475 ml) of the composition provides a unit dose of about 0.75 gram to about 20 grams, or about 1 gram to about 15 grams, or about 1.5 grams to about 12 grams, or about 2 grams to about 10 grams, of the exogenous beta-hydroxybutyrate to the mammal when consumed orally.

6. The aqueous beta-hydroxybutyric acid composition of claim 1, wherein the composition is a concentrated solution for addition to water, beverage, or food product in which the exogenous beta-hydroxybutyric acid has a concentration of about 6% w/v to about 55% w/v.

7. The aqueous beta-hydroxybutyric acid composition of claim 6, wherein the exogenous beta-hydroxybutyric acid has a concentration of about 8% w/v to about 55% w/v, or about 10% w/v to about 50% w/v, or about 12.5% w/v to about 45% w/v, or about 15% w/v to about 40% w/v.

8. The aqueous beta-hydroxybutyric acid composition of claim 1, wherein the composition contains less than 0.7%, or less than 0.6%, or less than 0.5%, or less than 0.4%, or less than 0.3%, or less than 0.2%, or less than 0.1%, of total beta-hydroxybutyrate salts and greater than 99.3%, or greater than 99.4%, or greater than 99.5%, or greater than 99.6%, or greater than 99.7%, or greater than 99.8%, or greater than 99.9%, of exogenous beta-hydroxybutyric acid by combined weight of the exogenous beta-hydroxybutyric acid and any beta-hydroxybutyrate salts.

9. The aqueous beta-hydroxybutyric acid composition of claim 1, wherein the exogenous beta-hydroxybutyric acid is a non-racemic mixture enriched with R-beta-hydroxybutyric acid and contains greater than 50% and less than 100% by enantiomeric equivalents of R-beta-hydroxybutyric acid and less than 50% and greater than 0% by enantiomeric equivalents of S-beta-hydroxybutyric acid.

10. The aqueous beta-hydroxybutyric acid composition of claim 1, wherein the composition is a gel and further comprises at least one gelling agent.

11. The aqueous beta-hydroxybutyric acid composition of claim 10, wherein the gelling agent is selected from gellan gum, pectin, agar, carrageenan, xanthan gum, alginate, starch, modified starch, gum Arabic, guar gum, locust bean gum, konjac, gum tragacanth, acacia gum, gum karaya, methyl cellulose, agar, pullulan, konjac, hydroxypropylmethyl cellulose, other cellulosic compounds, other polysaccharide gums, gelatin, collagen, casein, other proteins, silica fume, and milled chia seeds.

12. The aqueous beta-hydroxybutyric acid composition of claim 6, wherein the composition contains less water than is required to fully dissolve the exogenous beta-hydroxybutyric acid.

13. An aqueous beta-hydroxybutyric acid composition in the form of a nutritional beverage supplement for ingestion by oral delivery to provide exogenous ketone bodies that exogenously increase blood ketone level in a mammal, the composition comprising:
   water; and
   0.4% w/v to 5% w/v of exogenous beta-hydroxybutyric acid in monomeric form dissolved in the water to form an aqueous solution, wherein the composition is free or substantially free of beta-hydroxybutyrate salts so as to contain less than 0.8% of beta-hydroxybutyrate salts and greater than 99.2% of the exogenous beta-hydroxybutyric acid by combined weight of the exogenous beta-hydroxybutyric acid and any beta-hydroxybutyrate salt, wherein about 4 oz. (about 120 ml) to about 16 oz. (about 475 ml) of the composition when ingested by oral delivery provides a unit dose of about 0.5 gram to about 25 grams of total beta-hydroxybutyrate from the exogenous beta-hydroxybutyric acid and any beta-hydroxybutyrate salts, wherein the composition is free of 1,3-butanediol and ketone esters, wherein the composition has acidic pH and is formulated for ingestion by oral delivery as a nutritional beverage supplement to provide exogenous ketone bodies that exogenously increase blood ketone level in a mammal.

14. The aqueous beta-hydroxybutyric acid composition of claim 13, wherein the exogenous beta-hydroxybutyric acid has a concentration of about 0.6% w/v to about 4.5% w/v.

15. The aqueous beta-hydroxybutyric acid composition of claim 13, wherein the exogenous beta-hydroxybutyric acid has a concentration of about 0.9% w/v to about 4% w/v.

16. The aqueous beta-hydroxybutyric acid composition of claim 13, wherein about 4 oz. (about 120 ml) to about 16 oz. (about 475 ml) of the composition provides a unit dose of about 1 gram to about 15 grams of beta-hydroxybutyrate to the mammal when consumed orally.

17. The aqueous beta-hydroxybutyric acid composition of claim 13, wherein about 4 oz. (about 120 ml) to about 16 oz. (about 475 ml) of the composition provides a unit dose of about 1.5 grams to about 12 grams of beta-hydroxybutyrate to the mammal when consumed orally.

18. The aqueous beta-hydroxybutyric acid composition of claim 13, wherein about 4 oz. (about 120 ml) to about 16 oz. (about 475 ml) of the composition provides a unit dose of about 2 grams to about 10 grams of beta-hydroxybutyrate to the mammal when consumed orally.

19. The aqueous beta-hydroxybutyric acid composition of claim 13, wherein the composition is free of neutralizing base and beta-hydroxybutyrate salts and has a pH of less than 4.

20. An aqueous beta-hydroxybutyric acid composition in the form of a concentrated solution that can be added to water, beverage, or food to form an edible nutritional supplement for ingestion by oral delivery to provide exogenous ketone bodies that exogenously increase blood ketone level in a mammal, the composition comprising:
water; and
about 10% w/v to about 50% w/v of exogenous beta-hydroxybutyric acid in monomeric form at least partially dissolved in the water,
wherein the composition is free or substantially free of beta-hydroxybutyrate salts so as to contain less than 0.8% of beta-hydroxybutyrate salts and greater than 99.2% of exogenous beta-hydroxybutyric acid by combined weight of the exogenous beta-hydroxybutyric acid and any beta-hydroxybutyrate salts,
wherein the composition is free of 1,3-butanediol and ketone esters,
wherein the composition is a concentrated solution that when added to water, beverage, or food forms an edible nutritional supplement for ingestion by oral delivery to provide a unit dose of about 0.5 gram to about 25 grams of the exogenous beta-hydroxybutyric acid to provide exogenous ketone bodies that exogenously increase blood ketone level in a mammal.

21. The aqueous beta-hydroxybutyric acid composition of claim 20, wherein the composition is free of neutralizing base and beta-hydroxybutyrate salts and has a pH of less than 4.

22. An aqueous beta-hydroxybutyric acid composition formulated as a nutritional supplement, or for addition to water, beverage, or food product, for ingestion by oral delivery to provide exogenous ketone bodies that exogenously increase blood ketone level in a mammal, the composition comprising:
water;
0.4% w/v to 55% w/v of exogenous beta-hydroxybutyric acid in monomeric form at least partially dissolved in the water; and
at least one component selected from the group consisting of a fruit juice, beverage, food product, alcohol, flavorant, sweetener, glycerin, propylene glycol, 1,3-propandiol, essential oil, vitamin, mineral, central nervous system stimulant, nootropic, edible acid in addition to the beta-hydroxybutyric acid, vasodilator, muscle-promoting compound, silica, effervescing agent, cannabinoid, amino acid, gellan gum, pectin, agar, carrageenan, xanthan gum, alginate, starch, modified starch, gum Arabic, guar gum, locust bean gum, konjac, gum tragacanth, acacia gum, gum karaya, methyl cellulose, agar, pullulan, konjac, hydroxypropylmethyl cellulose, cellulosic compounds, other polysaccharide gums, gelatin, collagen, casein, proteins, silica fume, and milled chia seeds,
wherein the composition is free or substantially free of beta-hydroxybutyrate salts so as to contain less than 0.8% of total beta-hydroxybutyrate salts and greater than 99.2% of the exogenous beta-hydroxybutyric acid by combined weight of the exogenous beta-hydroxybutyric acid and any beta-hydroxybutyrate salts,
wherein the composition is free of 1,3-butanediol, and free of ketone esters,
wherein the composition is formulated as a nutritional supplement that provides a unit dose of about 0.5 gram to about 25 grams of the exogenous beta-hydroxybutyric acid to exogenously increase blood ketone level in a mammal.

23. The aqueous beta-hydroxybutyric acid composition of claim 22, wherein the composition is a dilute solution in which the exogenous beta-hydroxybutyric acid has a concentration of about 0.4% w/v to about 6% w/v.

24. The aqueous beta-hydroxybutyric acid composition of claim 22, wherein the composition is a concentrated solution for addition to water, beverage, or food product in which the exogenous beta-hydroxybutyric acid has a concentration of about 6% w/v to about 60% w/v.

25. The aqueous beta-hydroxybutyric acid composition of claim 1, wherein the composition is free of neutralizing base and beta-hydroxybutyrate salts and has a pH of less than 4.

26. The aqueous beta-hydroxybutyric acid composition of claim 22, wherein the composition is free of neutralizing base and beta-hydroxybutyrate salts and has a pH of less than 4.

27. An aqueous beta-hydroxybutyric acid composition formulated as a nutritional supplement to exogenously increase blood ketone level in a mammal, the composition comprising:
water;

0.4% w/v to 55% w/v of exogenous beta-hydroxybutyric acid in monomeric form at least partially dissolved in the water; and a gelling agent, wherein the composition is a gel, wherein the composition is free or substantially free of beta-hydroxybutyrate salts so as to contain less than 0.8% of total beta-hydroxybutyrate salts and greater than 99.2% of the exogenous beta-hydroxybutyric acid by combined weight of the exogenous beta-hydroxybutyric acid and any beta-hydroxybutyrate salts, wherein the composition is free of 1,3-butanediol and ketone esters, wherein the composition is a nutritional supplement that provides a unit dose of about 0.5 gram to about 25 grams of the exogenous beta-hydroxybutyric acid to exogenously increase blood ketone level in a mammal.

\* \* \* \* \*